US012683027B2

(12) United States Patent
Annangi et al.

(10) Patent No.: US 12,683,027 B2
(45) Date of Patent: Jul. 14, 2026

(54) DATA CANDIDATE QUERYING VIA EMBEDDINGS FOR DEEP LEARNING REFINEMENT

(71) Applicant: GE Precision Healthcare LLC, Wauwatosa, WI (US)

(72) Inventors: Pavan Annangi, Bangalore (IN); Deepa Anand, Bangalore (IN)

(73) Assignee: GE Precision Healthcare LLC, Waukesha, WI (US)

( * ) Notice: Subject to any disclaimer, the term of this patent is extended or adjusted under 35 U.S.C. 154(b) by 484 days.

(21) Appl. No.: 18/313,775

(22) Filed: May 8, 2023

(65) Prior Publication Data

US 2024/0379226 A1 Nov. 14, 2024

(51) Int. Cl.
*G06K 9/00* (2022.01)
*G06N 3/088* (2023.01)
*G06N 3/09* (2023.01)
*G06T 7/00* (2017.01)
*G16H 30/20* (2018.01)
*G16H 50/20* (2018.01)

(52) U.S. Cl.
CPC ............. *G16H 50/20* (2018.01); *G06N 3/088* (2013.01); *G06N 3/09* (2023.01); *G06T 7/0012* (2013.01); *G16H 30/20* (2018.01)

(58) Field of Classification Search
None
See application file for complete search history.

(56) References Cited

FOREIGN PATENT DOCUMENTS

WO WO-2022212771 A2 * 10/2022 ............. G16H 50/70
WO WO-2023023379 A1 * 2/2023 ........... G06F 40/258

OTHER PUBLICATIONS

Choe, J. et al. | "Content-based image retrieval by using deep learning for interstitial lung disease diagnosis with chest CT." Radiology, 302(1), 2022, pp. 187-197.2, https://doi.org.10.1148/radiol.2021204164, 11 pages.
Dilna, K.T., et al. | "Fibroid Segmentation in Ultrasound Uterus Images Using Wavelet Filter and Active Contour Model", from "Data Analytics and Management. Lecture Notes on Data Engineering and Communications Technologies." vol. 54. Springer, Singapore. https://doi.org/10.1007/978-981-15-8335-3_39, 9 pages.

* cited by examiner

*Primary Examiner* — Wei Wen Yang
(74) *Attorney, Agent, or Firm* — Amin, Turocy & Watson, LLP

(57) ABSTRACT

Systems/techniques that facilitate data candidate querying via embeddings for deep learning refinement are provided. In various embodiments, a system can access a test data candidate provided by a client, generate, via a first deep learning neural network, an inferencing output based on the test data candidate, and access feedback indicating whether the client accepts or rejects the inferencing output. In various aspects, the system can generate, via at least one second deep learning neural network, at least one embedding based on the test data candidate. In various instances, the system can, in response to the feedback indicating that the client rejects the inferencing output, identify, in a candidate-embedding dataset, one or more data candidates whose embeddings are within a threshold level of similarity to the at least one embedding and can retrain the first deep learning neural network based on the one or more data candidates.

20 Claims, 19 Drawing Sheets

300

TEST DATA
CANDIDATE 106

DEEP LEARNING
NEURAL NETWORK
104

INFERENCING
OUTPUT 202

FIG. 3

CANDIDATE-EMBEDDING DATASET 702

ANNOTATED DATA CANDIDATE 802(1) ⟷ EMBEDDING 804(1)

ANNOTATED DATA CANDIDATE 802(N) ⟷ EMBEDDING 804(N)

802

804

UNANNOTATED DATA CANDIDATE 806(1) ⟷ EMBEDDING 808(1)

UNANNOTATED DATA CANDIDATE 806(M) ⟷ EMBEDDING 808(M)

806

808

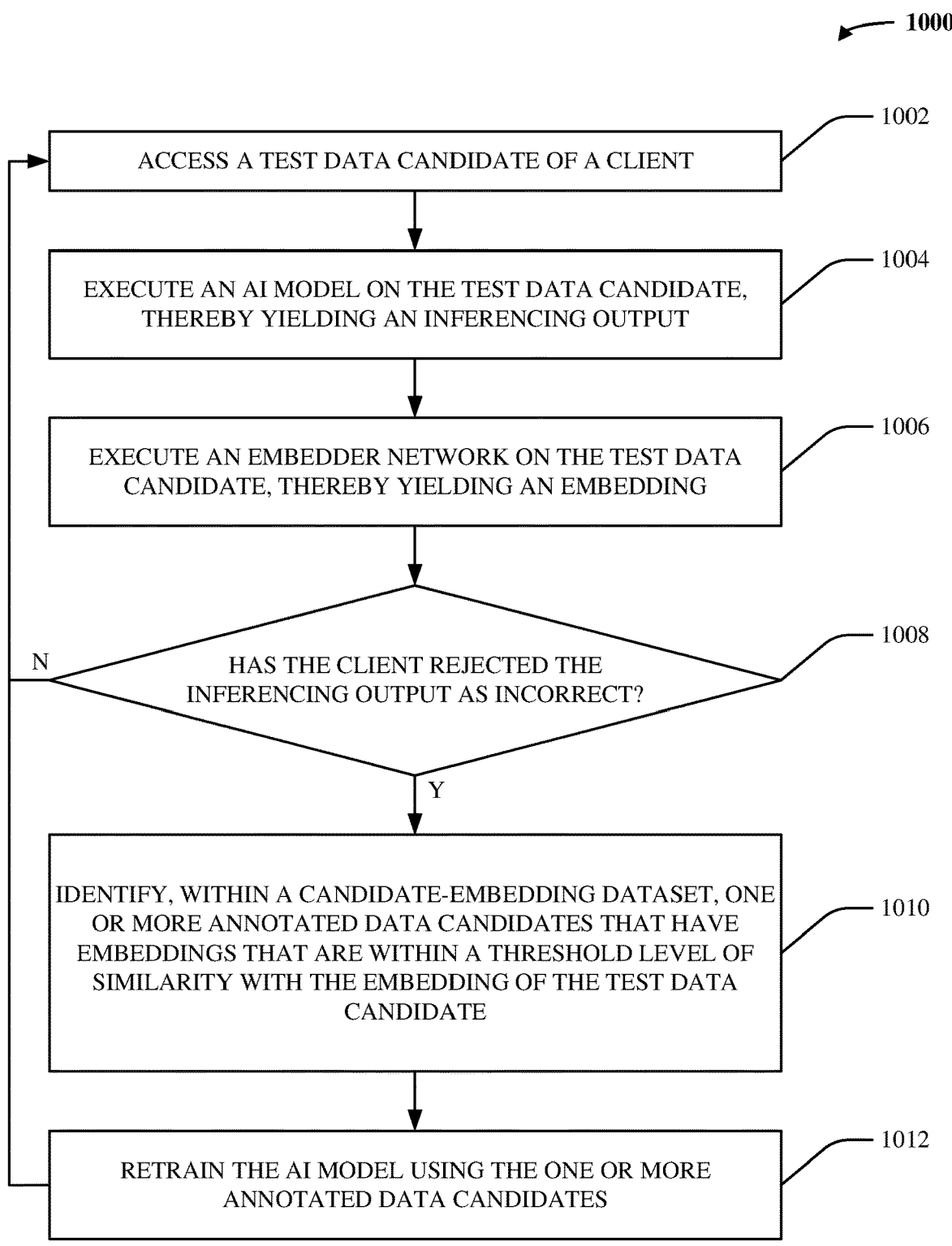

1000

1002
ACCESS A TEST DATA CANDIDATE OF A CLIENT

1004
EXECUTE AN AI MODEL ON THE TEST DATA CANDIDATE, THEREBY YIELDING AN INFERENCING OUTPUT

1006
EXECUTE AN EMBEDDER NETWORK ON THE TEST DATA CANDIDATE, THEREBY YIELDING AN EMBEDDING

1008
HAS THE CLIENT REJECTED THE INFERENCING OUTPUT AS INCORRECT?
N
Y

1010
IDENTIFY, WITHIN A CANDIDATE-EMBEDDING DATASET, ONE OR MORE ANNOTATED DATA CANDIDATES THAT HAVE EMBEDDINGS THAT ARE WITHIN A THRESHOLD LEVEL OF SIMILARITY WITH THE EMBEDDING OF THE TEST DATA CANDIDATE

1012
RETRAIN THE AI MODEL USING THE ONE OR MORE ANNOTATED DATA CANDIDATES

ANNOTATED DATA
CANDIDATE 1102

EMBEDDER NEURAL
NETWORK 402

EMBEDDING 1104

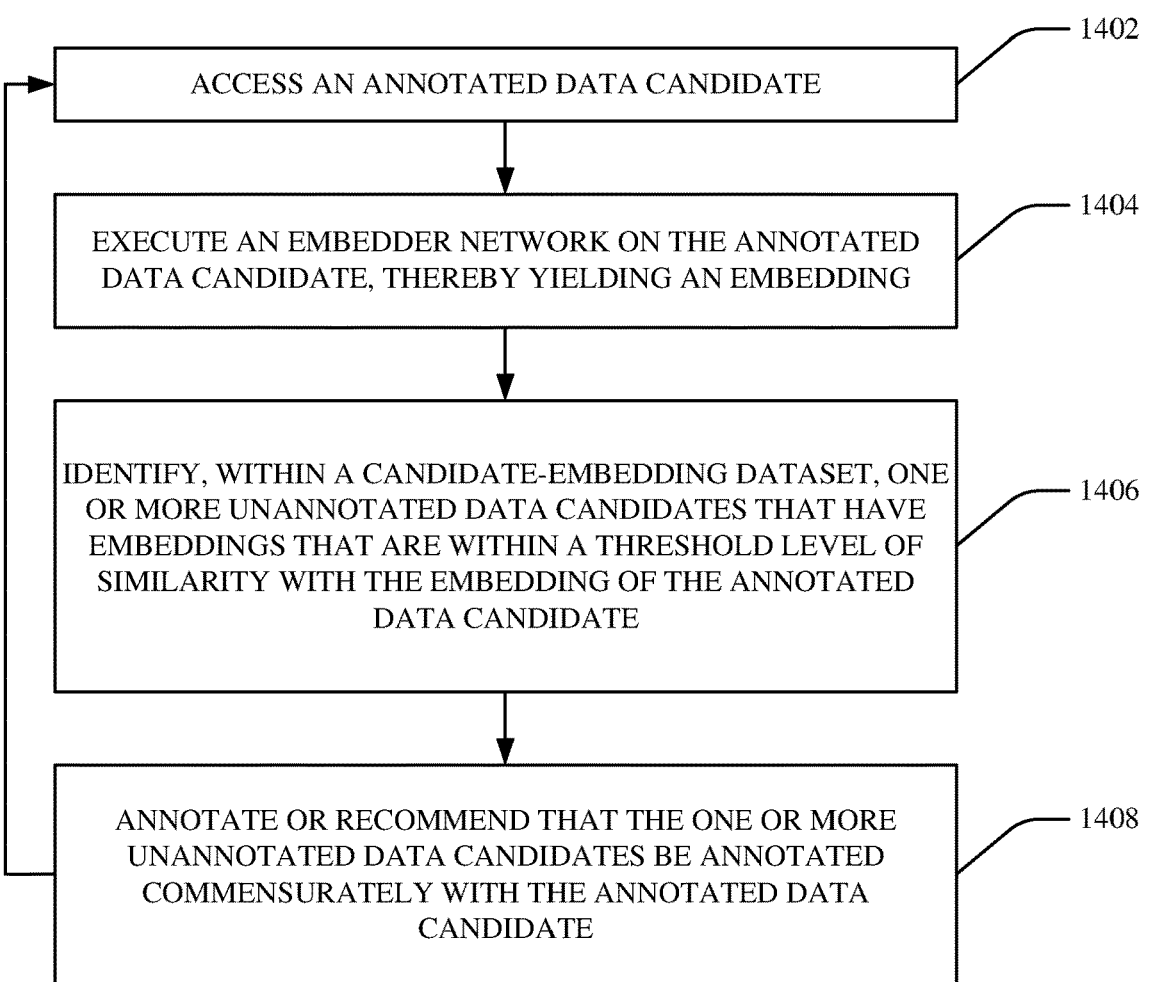

ACCESS AN ANNOTATED DATA CANDIDATE — 1402

EXECUTE AN EMBEDDER NETWORK ON THE ANNOTATED DATA CANDIDATE, THEREBY YIELDING AN EMBEDDING — 1404

IDENTIFY, WITHIN A CANDIDATE-EMBEDDING DATASET, ONE OR MORE UNANNOTATED DATA CANDIDATES THAT HAVE EMBEDDINGS THAT ARE WITHIN A THRESHOLD LEVEL OF SIMILARITY WITH THE EMBEDDING OF THE ANNOTATED DATA CANDIDATE — 1406

ANNOTATE OR RECOMMEND THAT THE ONE OR MORE UNANNOTATED DATA CANDIDATES BE ANNOTATED COMMENSURATELY WITH THE ANNOTATED DATA CANDIDATE — 1408

FIG. 14

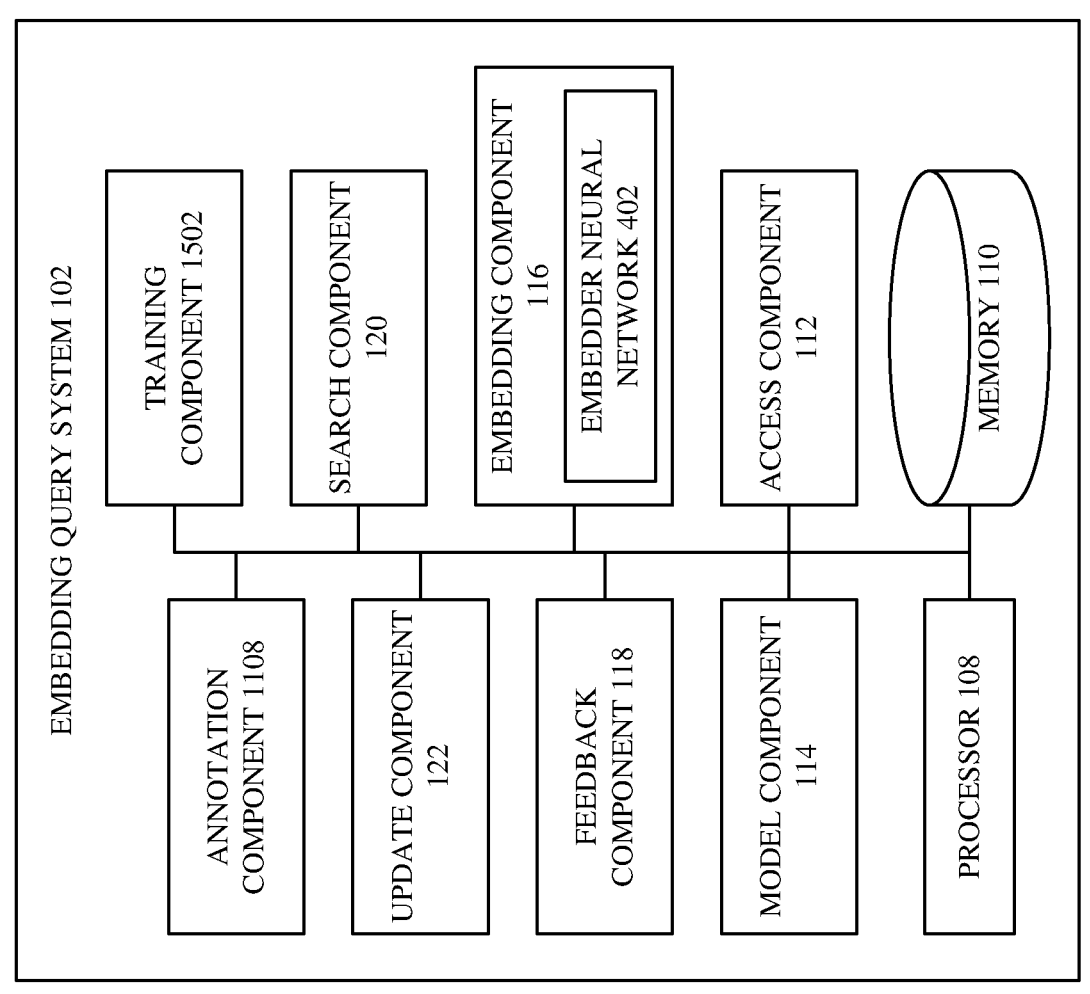
FIG. 15

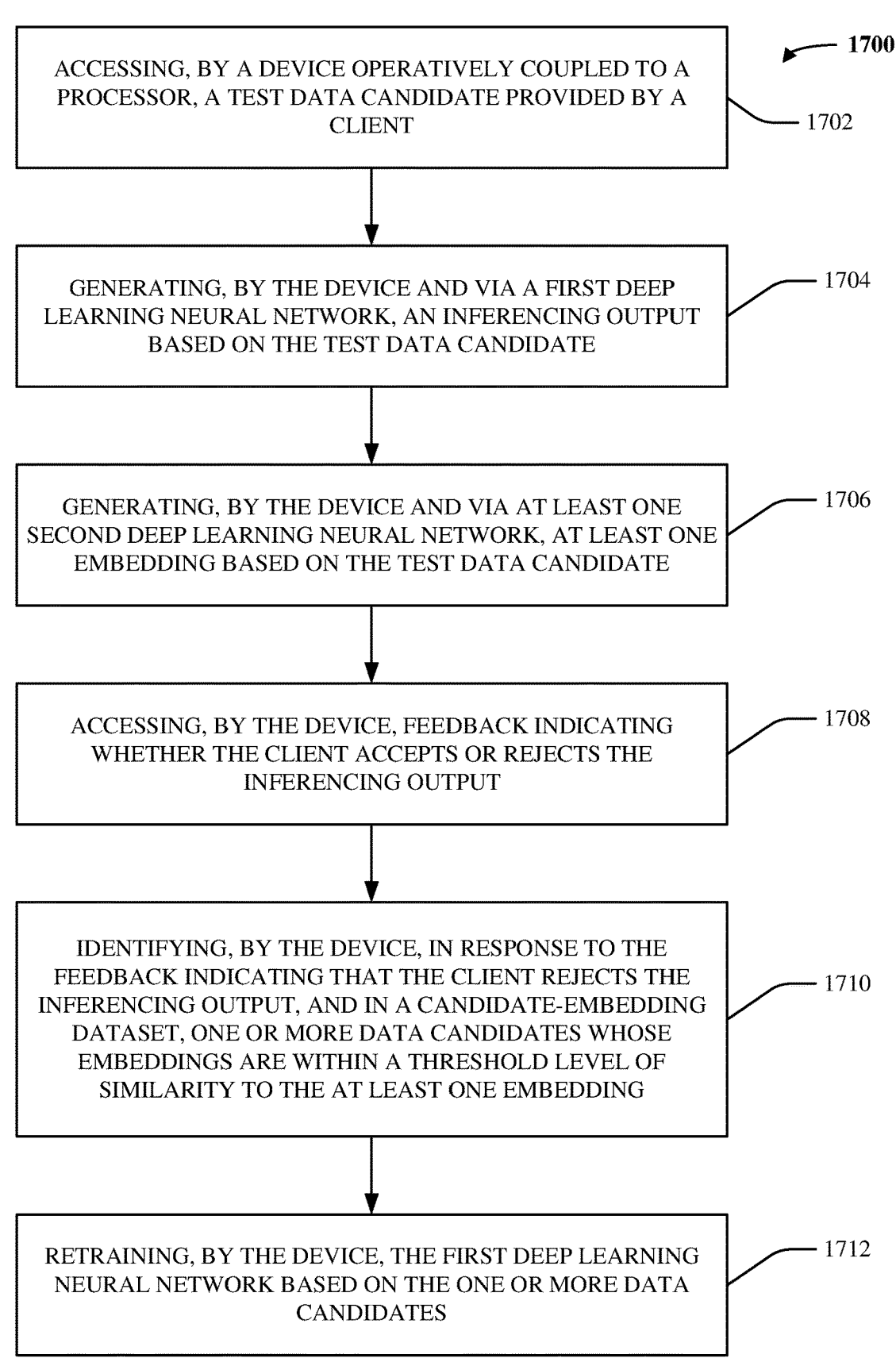

ACCESSING, BY A DEVICE OPERATIVELY COUPLED TO A PROCESSOR, A TEST DATA CANDIDATE PROVIDED BY A CLIENT
— 1702

— 1700

GENERATING, BY THE DEVICE AND VIA A FIRST DEEP LEARNING NEURAL NETWORK, AN INFERENCING OUTPUT BASED ON THE TEST DATA CANDIDATE
— 1704

GENERATING, BY THE DEVICE AND VIA AT LEAST ONE SECOND DEEP LEARNING NEURAL NETWORK, AT LEAST ONE EMBEDDING BASED ON THE TEST DATA CANDIDATE
— 1706

ACCESSING, BY THE DEVICE, FEEDBACK INDICATING WHETHER THE CLIENT ACCEPTS OR REJECTS THE INFERENCING OUTPUT
— 1708

IDENTIFYING, BY THE DEVICE, IN RESPONSE TO THE FEEDBACK INDICATING THAT THE CLIENT REJECTS THE INFERENCING OUTPUT, AND IN A CANDIDATE-EMBEDDING DATASET, ONE OR MORE DATA CANDIDATES WHOSE EMBEDDINGS ARE WITHIN A THRESHOLD LEVEL OF SIMILARITY TO THE AT LEAST ONE EMBEDDING
— 1710

RETRAINING, BY THE DEVICE, THE FIRST DEEP LEARNING NEURAL NETWORK BASED ON THE ONE OR MORE DATA CANDIDATES
— 1712

FIG. 17

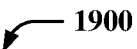
1900
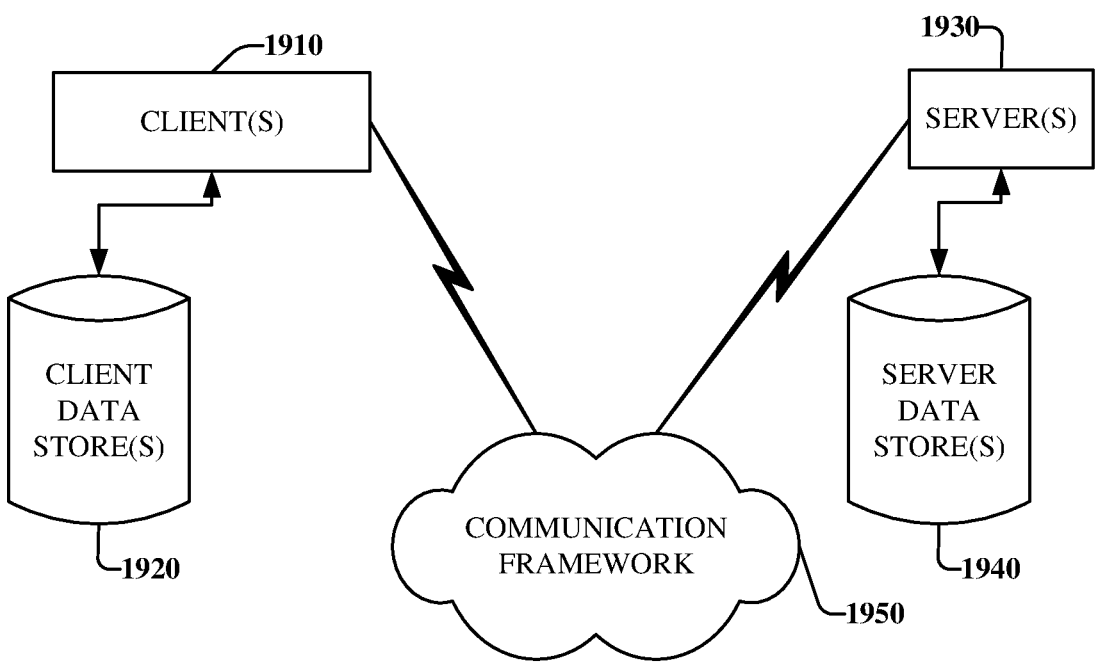
1910
CLIENT(S)
1930
SERVER(S)
CLIENT
DATA
STORE(S)
1920
COMMUNICATION
FRAMEWORK
1950
SERVER
DATA
STORE(S)
1940
FIG. 19

DATA CANDIDATE QUERYING VIA EMBEDDINGS FOR DEEP LEARNING REFINEMENT

TECHNICAL FIELD

The subject disclosure relates generally to deep learning, and more specifically to data candidate querying via embeddings for deep learning refinement.

BACKGROUND

A deep learning neural network can be trained, in supervised fashion on annotated data, to perform an inferencing task. After being trained, the deep learning neural network can be deployed in any suitable operational context, so as to perform the inferencing task on unannotated or test data. If the deep learning neural network is found to have inaccurately performed the inferencing task on any given data during deployment, retraining of the deep learning neural network can be warranted. In particular, it can be desirable to retrain the deep learning neural network on annotated data that is substantively-similar to the given data that caused the deep learning neural network to fail. Unfortunately, due to privacy concerns or regulations, the given data that caused the deep learning neural network to fail can become unavailable after inferencing, which means that similar annotated data cannot be identified for retraining. Even if the given data that caused the deep learning neural network to fail is available after inferencing, existing techniques involve manually selecting annotated data that visually appear to be similar to the given data. Such manual selection is excessively time-consuming and error-prone.

Accordingly, systems or techniques that can promote deep learning retraining or refinement by automatically identifying annotated data that is similar to failure data, even when such failure data is no longer available, can be considered as desirable.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate data candidate querying via embeddings for deep learning refinement are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access a test data candidate provided by a client. In various aspects, the computer-executable components can comprise a model component that can generate, via a first deep learning neural network, an inferencing output based on the test data candidate. In various instances, the computer-executable components can comprise an embedding component that can generate, via at least one second deep learning neural network, at least one embedding based on the test data candidate. In various cases, the computer-executable components can comprise a feedback component that can access feedback indicating whether the client accepts or rejects the inferencing output. In various aspects, the computer-executable components can comprise a search component that, in response to the feedback indicating that the client rejects the inferencing output, can identify, in a candidate-embedding dataset, one or more data candidates whose embeddings are within a threshold level of similarity to the at least one embedding. In various instances, the computer-executable components can comprise an update component that can retrain the first deep learning neural network based on the one or more data candidates.

According to one or more embodiments, a computer-implemented method is provided. In various embodiments, the computer-implemented method can comprise accessing, by a device operatively coupled to a processor, a scanned medical image provided by a client. In various aspects, the computer-implemented method can comprise generating, by the device and via a first deep learning neural network, a diagnostic or prognostic output based on the scanned medical image. In various instances, the computer-implemented method can comprise generating, by the device and via at least one second deep learning neural network, at least one embedding based on the scanned medical image. In various cases, the computer-implemented method can comprise accessing, by the device, feedback indicating whether the client accepts or rejects the diagnostic or prognostic output. In various aspects, the computer-implemented method can comprise identifying, by the device, in response to the feedback indicating that the client rejects the diagnostic or prognostic output, and in an image-embedding dataset, one or more medical images whose embeddings are within a threshold level of similarity to the at least one embedding. In various instances, the computer-implemented method can comprise retraining, by the device, the first deep learning neural network based on the one or more medical images.

According to one or more embodiments, a computer program product for facilitating data candidate querying via embeddings for deep learning refinement is provided. In various embodiments, the computer program product can comprise a non-transitory computer-readable memory having program instructions embodied therewith. In various aspects, the program instructions can be executable by a processor to cause the processor to access an annotated data candidate. In various instances, the program instructions can be further executable to cause the processor to generate, via at least one deep learning neural network, at least one embedding based on the annotated data candidate. In various cases, the program instructions can be further executable to cause the processor to identify, in a candidate-embedding dataset, one or more unannotated data candidates whose embeddings are within a threshold level of similarity to the at least one embedding. In various aspects, the program instructions can be further executable to cause the processor to generate an electronic message recommending that the one or more unannotated data candidates be annotated in accordance with the annotated data candidate.

DESCRIPTION OF THE DRAWINGS

FIG. 3 illustrates an example, non-limiting block diagram showing how an inferencing output can be obtained in accordance with one or more embodiments described herein.

FIG. 10 illustrates a flow diagram of an example, non-limiting computer-implemented method that facilitates data candidate querying via embeddings for deep learning refinement in accordance with one or more embodiments described herein.

FIG. 12 illustrates an example, non-limiting block diagram showing how an embedder neural network can generate an embedding for an annotated data candidate in accordance with one or more embodiments described herein.

FIG. 14 illustrates a flow diagram of an example, non-limiting computer-implemented method that facilitates data candidate querying via embeddings for deep learning refinement in accordance with one or more embodiments described herein.

FIG. 15 illustrates a block diagram of an example, non-limiting system including a training component that facilitates data candidate querying via embeddings for deep learning refinement in accordance with one or more embodiments described herein.

FIG. 17 illustrates a flow diagram of an example, non-limiting computer-implemented method that facilitates data candidate querying via embeddings for deep learning refinement in accordance with one or more embodiments described herein.

FIG. 19 illustrates an example networking environment operable to execute various implementations described herein.

DETAILED DESCRIPTION

Figure 1:
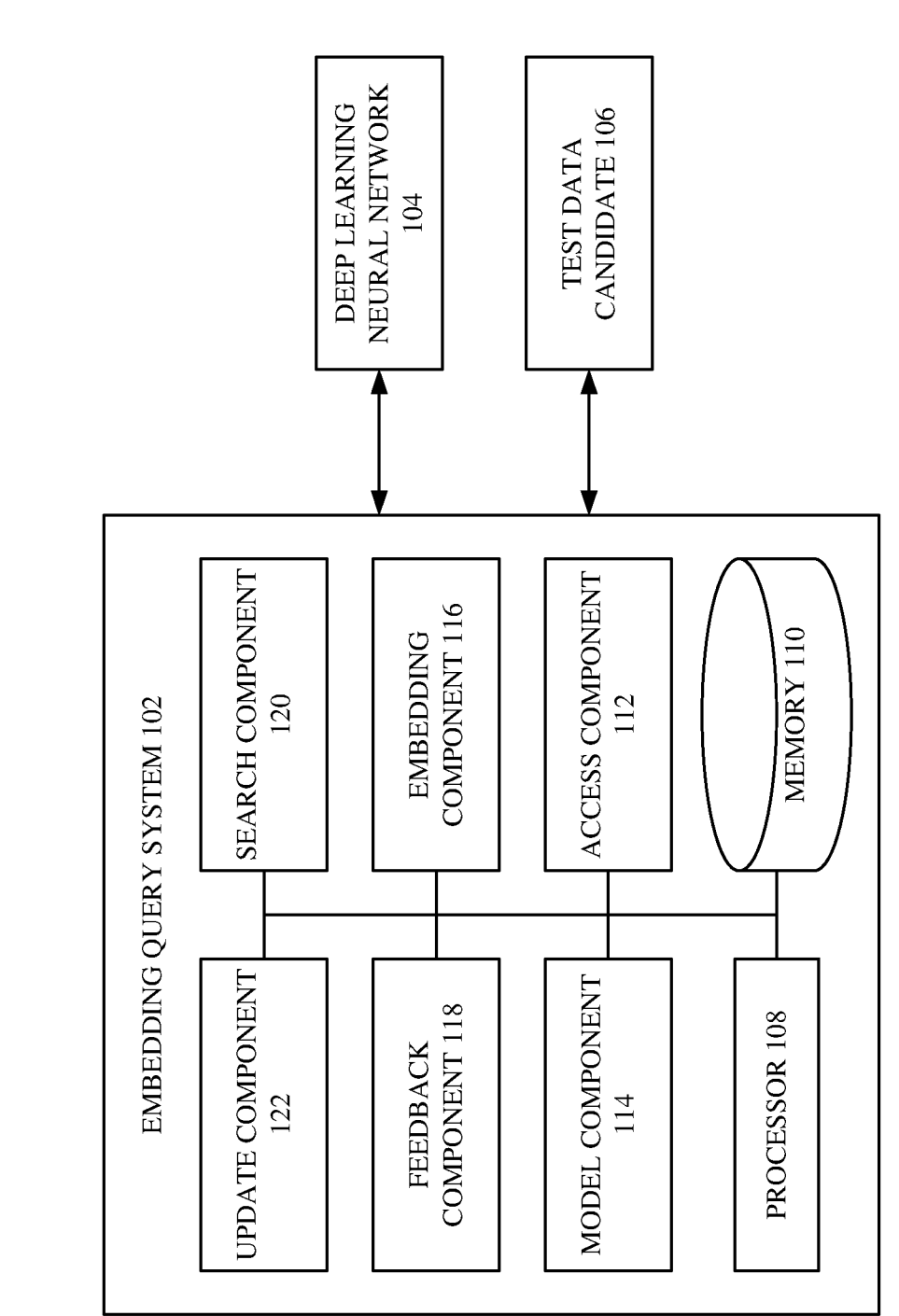
FIG. 1 illustrates a block diagram of an example, non-limiting system that facilitates data candidate querying via embeddings for deep learning refinement in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A deep learning neural network can be trained, in supervised fashion on annotated data (e.g., on data candidates for which ground-truth annotations are known or available), to perform an inferencing task (e.g., classification, segmentation, regression). After being trained, the deep learning neural network can be deployed in any suitable operational context, so as to perform the inferencing task on unannotated or test data. For example, the deep learning neural network can be deployed in a medical or clinical operational context, so as to generate classification labels, segmentation masks, or regressions regarding medical patients. As another example, the deep learning neural network can be deployed in a financial operational context, so as to generate classification labels, segmentation masks, or regressions regarding consumers or purchasers. As yet another example, the deep learning neural network can be deployed in a computer vision operational context, so as to generate classification labels, segmentation masks, or regressions regarding autonomous vehicles or security camera footage.

Despite being trained, the deep learning neural network can nevertheless fail to accurately or correctly perform the inferencing task during deployment. If the deep learning neural network is found (e.g., through client feedback) to have inaccurately performed the inferencing task on any given data during deployment, retraining of the deep learning neural network can be warranted. Indeed, such retraining can be considered as an iteration of continuous, continual, or on-going model refinement (e.g., sometimes referred to as MLops). In particular, it can be desired to retrain the deep learning neural network on annotated data that is substantively-similar to the given data that caused the deep learning neural network to fail. Such retraining can be considered as focusing on or otherwise rectifying an identified failure mode of the deep learning neural network.

Unfortunately, due to privacy concerns (e.g., clients often desire to protect or preserve their sensitive data) or regulations (e.g., laws often restrict the sharing or distribution of sensitive data), the given data that caused the deep learning neural network to fail can become unavailable after inferencing. Such unavailability of the given data can make it difficult or impossible to identify substantively-similar annotated data for retraining. Even if the given data that caused the deep learning neural network to fail is available after inferencing, existing techniques involve manually selecting (e.g., by subject matter experts or technicians) annotated data that visually appear to be similar to the given data. Unfortunately, such manual selection is excessively time-consuming and error-prone.

Accordingly, systems or techniques that can promote deep learning retraining or refinement (e.g., that can promote MLops) by automatically identifying annotated data that is similar to failure data, even when such failure data is no longer available, can be considered as desirable.

Various embodiments described herein can address one or more of these technical problems. One or more embodiments described herein can include systems, computer-implemented methods, apparatus, or computer program products that can facilitate data candidate querying via embeddings for deep learning refinement. In other words, the inventors of various embodiments described herein devised various techniques that utilize embeddings (e.g., latent vector representations) to automatically identify annotated data that is substantively-similar to failure data. In particular, when given any test data candidate, the inferencing task can be performed on the test data candidate, and an embedding can be generated as described herein based on the test data candidate. Moreover, there can be a candidate-embedding store that includes various annotated data candidates each corresponding to a respective embedding. Now, suppose that a client indicates that the inferencing task was performed inaccurately on the test data candidate, and suppose that the test data candidate is no longer available due to privacy. In such case, the embedding of the test data candidate can nevertheless be available (e.g., the embedding can be considered as a compressed, scrambled, or not-readily-interpretable version of the test data candidate that does not invoke privacy concerns). Accordingly, the embedding of the test data candidate be used to query the candidate-embedding store in search of one or more similar embeddings. Whatever annotated data candidates correspond to such one or more similar embeddings can be considered as being substantively-similar to the test data candidate. Thus, retraining can be performed based on such one or more annotated data candidates. In this way, annotated data that is substantively-similar to failure data can be automatically identified, even if such failure data is no longer available due to privacy concerns or regulations. In other words, various embodiments described herein can help to facilitate MLops (e.g., continuous, continual, or on-going model refinement).

Various embodiments described herein can be considered as a computerized tool (e.g., any suitable combination of computer-executable hardware or computer-executable software) that can facilitate data candidate querying via embeddings for deep learning refinement. In various aspects, such computerized tool can comprise an access component, a model component, an embedding component, a feedback component, a search component, or an update component.

In various embodiments, there can be a deep learning neural network. In various aspects, the deep learning neural network can exhibit any suitable internal architecture. For example, the deep learning neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the deep learning neural network can include any suitable numbers of neurons in various layers (e.g., different layers can have the same or different numbers of neurons as each other). As yet another example, the deep learning neural network can include any suitable activation functions (e.g., softmax, sigmoid, hyperbolic tangent, rectified linear unit) in various neurons (e.g., different neurons can have the same or different activation functions as each other). As still another example, the deep learning neural network can include any suitable interneuron connections or interlayer connections (e.g., forward connections, skip connections, recurrent connections).

Regardless of its internal architecture, the deep learning neural network can be configured to perform an inferencing task on data candidates. In various aspects, a data candidate can be any suitable electronic data exhibiting any suitable format, size, or dimensionality. As some non-limiting examples, a data candidate can be an image, a video, an audio waveform, or a textual document. In various instances, the inferencing task can be any suitable computational, predictive task that can be performed on or with respect to a data candidate. As some non-limiting examples, the inferencing task can be classification, segmentation, or regression (e.g., denoising, resolution enhancement). In various cases, the deep learning neural network can have been trained in supervised fashion to perform the inferencing task.

In various embodiments, there can be a test data candidate. In various aspects, the test data candidate can be any suitable data candidate provided, supplied, or otherwise submitted by any suitable client (e.g., human, computer, or otherwise). In various instances, the client can desire the inferencing task to be performed on or otherwise with respect to the test data candidate. In various cases, the client can have various privacy or security concerns regarding the test data candidate (e.g., the client can desire that the test data candidate not be shared or distributed with other entities). Accordingly, the test data candidate can be considered as being available to the computerized tool described herein for a temporary, short, or otherwise limited temporal window during which the inferencing task is to be performed.

It can be the case that the deep learning neural network incorrectly performs the inferencing task on the test data candidate. In such situations, it can be desired to retrain the deep learning neural network using annotated data candidates that are substantively-similar to the test data candidate. In various instances, the computerized tool can facilitate such retraining as described herein.

In various embodiments, the access component of the computerized tool can electronically receive or otherwise electronically access the deep learning neural network or the test data candidate. In some aspects, the access component can electronically retrieve the deep learn neural network or the test data candidate from any suitable centralized or decentralized data structures (e.g., graph data structures, relational data structures, hybrid data structures), whether remote from or local to the access component. In any case, the access component can electronically obtain or access the deep learning neural network or the test data candidate, such that other components of the computerized tool can electronically interact with (e.g., read, write, edit, copy, manipulate) the deep learning neural network or with the test data candidate.

In various embodiments, the model component of the computerized tool can electronically generate an inferencing output, by executing the deep learning neural network on the test data candidate. More specifically, the model component can feed the test data candidate to an input layer of the deep learning neural network, the test data candidate can complete a forward pass through one or more hidden layers of the deep learning neural network, and an output layer of the deep learning neural network can compute the inferencing output based on activations from the one or more hidden layers of the deep learning neural network.

In various aspects, the inferencing output can be any suitable electronic data whose format, size, or dimensionality can depend upon the inferencing task. For example, if the inferencing task is classification, then the inferencing output can be a classification label that the deep learning neural network has predicted or inferred corresponds to the test data candidate. As another example, if the inferencing task is segmentation, then the inferencing output can be a segmentation mask that the deep learning neural network has predicted or inferred corresponds to the test data candidate. As yet another example, if the inferencing task is regression, then the inferencing output can be a regression result (e.g., one or more continuously variable scalars) that the deep learning neural network has predicted or inferred corresponds to the test data candidate.

In various embodiments, the embedding component of the computerized tool can store, maintain, control, or otherwise access an embedder neural network. In various aspects, the embedder neural network can exhibit any suitable internal architecture. For example, the embedder neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the embedder neural network can include any suitable numbers of neurons in various layers (e.g., different layers can have the same or different numbers of neurons as each other). As yet another example, the embedder neural network can include any suitable activation functions (e.g., softmax, sigmoid, hyperbolic tangent, rectified linear unit) in various neurons (e.g., different neurons can have the same or different activation functions as each other). As still another example, the embedder neural network can include any suitable interneuron connections or interlayer connections (e.g., forward connections, skip connections, recurrent connections).

Regardless of its internal architecture, the embedder neural network can be configured to compress data candidates into embeddings. Accordingly, in various aspects, the embedding component can electronically generate an embedding for the test data candidate, by executing the embedder neural network on the test data candidate. In particular, the embedding component can feed the test data candidate to an input layer of the embedder neural network, the test data candidate can complete a forward pass through one or more hidden layers of the embedder neural network, and an output layer of the embedder neural network can compute the inferencing output based on activations from the one or more hidden layers of the embedder neural network.

In any case, the embedding can be considered as a latent vector representation of the test data candidate. Accordingly, the embedding can be any suitable electronic data whose format, size, or dimensionality is smaller (e.g., many orders of magnitude smaller) than that of the test data candidate but that nevertheless indicates or conveys (e.g., albeit in a hidden fashion) substantive content of the test data candidate. For example, the test data candidate can be an image having hundreds of thousands of pixels, and the embedding can be a vector having merely a few dozen elements; however, those few dozen elements can collectively represent, indicate, or otherwise capture at least some of whatever substantive content is illustrated by those hundreds of thousands of pixels. Thus, the embedder neural network can, in various instances, be considered as having compressed the test data candidate into the embedding.

Note that the embedding can lack any apparent or clear relationship to the test data candidate, as if the embedding were an encrypted or scrambled version of the test data candidate. In other words, a third-party could not easily or readily guess or recreate the substantive content of the test data candidate by considering the embedding alone. So, the embedding can, in various cases, be considered as preserving the privacy of the test data candidate (e.g., the embedding can be stored, shared, or distributed without compromising the security of the test data candidate).

Furthermore, note that, as mentioned above, it can be the case that the computerized tool has a temporary, short, or otherwise limited temporal window during which the inferencing task is to be performed on the test data candidate. After that temporal window elapses, the test data candidate can become unavailable to the computerized tool. Thus, during that temporal window, the model component can execute the deep learning neural network on the test data candidate, thereby yielding the inferencing output. Likewise, during that temporal window, the embedding component can execute the embedder neural network on the test data candidate, thereby yielding the embedding. Although the test data candidate can become unavailable after that temporal window elapses, the embedding, in contrast, can remain available after that temporal window elapses.

In various embodiments, the feedback component of the computerized tool can receive, retrieve, or otherwise access feedback pertaining to the inferencing output. In various aspects, the feedback can be any suitable electronic data indicating, conveying, or representing whether the client accepts or rejects the inferencing output. If the feedback indicates that the client accepts or otherwise approves the inferencing output, this can be interpreted to mean that the deep learning neural network has correctly or accurately performed the inferencing task on the test data candidate. Instead, if the feedback indicates that the client rejects or otherwise disapproves the inferencing output, this can be interpreted to mean that the deep learning neural network has incorrectly or inaccurately performed the inferencing task on the test data candidate. In various cases, the feedback component can obtain the feedback from the client using any suitable human-computer interface device (e.g., keyboard, keypad, touchscreen, voice-command).

In various embodiments, if the feedback indicates that the client accepts or approves the inferencing output, the computerized tool can refrain from taking further action with respect to the test data candidate. However, if the feedback instead indicates that the client rejects or disapproves the inferencing output, the search component and the update component of the computerized tool can take further action.

In particular, the search component can store, maintain, control, or otherwise access a candidate-embedding dataset. In various aspects, the candidate-embedding dataset can comprise a set of annotated data candidates, where an annotated data candidate can be any suitable data candidate (e.g., having the same format, size, or dimensionality as the test data candidate) for which a respective ground-truth annotation (e.g., ground-truth classification label, ground-truth segmentation mask, ground-truth regression result) is known. In various aspects, the candidate-embedding data can also comprise a set of unannotated data candidates, where an unannotated data candidate can be any suitable data candidate (e.g., having the same format, size, or dimensionality as the test data candidate) for which a respective ground-truth annotation is not known. In various instances, each data candidate (e.g., both annotated and unannotated) within the candidate-embedding dataset can correspond to a respective or unique embedding. Indeed, in various cases, the embedder neural network can have (e.g., at any suitable prior time) been executed on each of those annotated and unannotated data candidates, thereby yielding those embeddings.

In various aspects, in response to the feedback indicating that the client has rejected or disapproved the inferencing output (e.g., in response to the test data candidate being a failure mode of the deep learning neural network), the search component can query the candidate-embedding dataset for one or more annotated data candidates whose embeddings are within any suitable threshold margin of similarity to the embedding of the test data candidate. In various instances, the search component can facilitate such query via any suitable metric for comparing embeddings. As an example, the search component can compare embeddings using cosine similarity (e.g., each embedding can be considered as a vector, and thus a cosine similarity value can be computed between any two of such vectors). As another example, the search component can compare embeddings using Euclidean distance (e.g., each embedding can be considered as a vector, and thus a Euclidean distance value can be computed between any two of such vectors). In any case, the search component can identify, within the candidate-embedding dataset, one or more annotated data candidates whose embeddings are sufficiently similar (e.g., are within a threshold margin of cosine similarity or a threshold margin of Euclidean distance) to the embedding of the test data candidate. Accordingly, such one or more annotated data candidates can be considered as having substantive content that is similar to that of the test data candidate. Note that such querying of the candidate-embedding dataset can be performed even after the test data candidate is no longer available to the computerized tool (e.g., the embedding of the test data candidate can be available even if the test data candidate itself is no longer available).

In various embodiments, the update component of the computerized tool can retrain (e.g., using any suitable batch sizes, any suitable training termination criteria, or any suitable error or loss functions) the deep learning neural network based on the one or more annotated data candidates. For example, the update component can: execute the deep learning neural network on such one or more annotated data candidates, thereby yielding one or more inferred or predicted outputs (e.g., one or more inferred or predicted classification labels, inferred or predicted segmentation masks, or inferred or predicted regression results); compute one or more errors or losses (e.g., mean absolute error (MAE), mean squared error (MSE), cross-entropy) between those one or more inferred or predicted outputs and whatever ground-truth annotations correspond to the one or more annotated data candidates; and incrementally update, via backpropagation (e.g., stochastic gradient descent), internal parameters (e.g., weight matrices, bias values, convolutional kernels) of the deep learning neural network based on the one or more errors or losses. Such retraining can be considered as refining the deep learning neural network so that it can more accurately handle substantive content like that of the test data candidate in the future.

Accordingly, the computerized tool can, in various embodiments, be considered as automatically refining or retraining the deep learning neural network so as to address an identified failure mode indicated by client feedback. Such refinement/retraining can be facilitated, notwithstanding that the specific data which caused such failure mode (e.g., the test data candidate) can be no longer available (e.g., due to privacy restrictions) at the time of such refinement/retraining.

However, the aforementioned is a mere non-limiting example of the computerized tool. In some embodiments, rather than there being the test data candidate, there can instead be an annotated data candidate. In various aspects, the annotated data candidate can be any suitable data candidate for which a respective ground-truth annotation is known. As mentioned above, the candidate-embedding dataset can include not just annotated data candidates but also unannotated data candidates. In various instances, the computerized tool can, as described herein, leverage the annotated data candidate to help streamline annotation generation for the unannotated data candidates in the candidate-embedding dataset.

In various embodiments, the access component can receive, retrieve, obtain, or otherwise access, from any suitable source, the annotated data candidate. In various aspects, the model component, the feedback component, and the update component can refrain from taking action with respect to the annotated data candidate. Instead, the embedding component and the search component can take action with respect to the annotated data candidate. Moreover, the computerized tool can further comprise an annotation component that also take action with respect to the annotated data candidate.

Indeed, in various aspects, the embedding component can execute the embedder neural network on the annotated data candidate, thereby yielding another embedding. Just as described above, the another embedding can be considered as a latent vector representation of the annotated data candidate. In various instances, the search component can query the candidate-embedding dataset for one or more unannotated data candidates whose embeddings are within any suitable threshold margin of similarity to the another embedding of the annotated data candidate. As above, the search component can facilitate such query via any suitable metric for comparing embeddings (e.g., cosine similarity, Euclidean distance). In any case, the one or more unannotated data candidates can be considered as having substantive content that is sufficiently similar to that of the annotated data candidate. Thus, in various cases, the annotation component of the computerized tool can generate, render, or transmit any suitable electronic message that suggests or recommends that those one or more unannotated data candidates be annotated similarly, commensurately, or otherwise in conjunction with the annotated data candidate. In fact, in some cases, the annotation component can automatically annotate the one or more unannotated data candidates using the ground-truth annotation of the annotated data candidate (e.g., if the inferencing task is classification, then the annotation component can automatically assign to the one or more unannotated data candidates the same ground-truth classification label that the annotated data candidate has).

In this way, the computerized tool can, in various embodiments, be considered as helping to automate or streamline annotation procedures for currently unannotated data candidates.

In order for the embeddings described herein to be accurate, the embedder neural network can first undergo training. Accordingly, the computerized tool can comprise a training component, and the training component can train the embedder neural network in any suitable fashion. In particular, the training component can train the embedder neural network in unsupervised fashion using an encoder-decoder deep learning framework, as described herein.

In various aspects, in addition to the embedder neural network, there can be another deep learning neural network. In various instances, the another deep learning neural network can exhibit any suitable internal architecture. For example, the another deep learning neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the another deep learning neural network can include any suitable numbers of neurons in various layers (e.g., different layers can have the same or different numbers of neurons as each other). As yet another example, the another deep learning neural network can include any suitable activation functions (e.g., softmax, sigmoid, hyperbolic tangent, rectified linear unit) in various neurons (e.g., different neurons can have the same or different activation functions as each other). As still another example, the another deep learning neural network can include any suitable interneuron connections or inter-layer connections (e.g., forward connections, skip connections, recurrent connections).

Regardless of its internal architecture, the another deep learning neural network can be configured to perform an inverse function as the embedder neural network. That is, the embedder neural network can be configured to generate embeddings (e.g., latent vectors) of inputted data candidates, whereas the another deep learning neural network can instead be configured to generate data candidates based on inputted embeddings (e.g., from inputted latent vectors).

At the start of training, the trainable internal parameters (e.g., weight matrices, bias values, convolutional kernels) of the embedder neural network and of the another deep learning neural network can be randomly initialized.

In various aspects, the training component can select, obtain, or otherwise access any suitable data candidate. In various instances, the training component can execute the embedder neural network on the selected data candidate, and such execution can cause the embedder neural network to produce a first output. More specifically, the training component can feed the selected data candidate to the input layer of the embedder neural network, the selected data candidate can complete a forward pass through the one or more hidden layers of the embedder neural network, and the output layer of the embedder neural network can compute or calculate the first output based on activations produced by the one or more hidden layers of the embedder neural network.

Note that, in various cases, the format, size, or dimensionality of the first output can be controlled or otherwise determined by the number or arrangement of neurons (or by the number or arrangement of other internal parameters, such as convolutional kernels) that are in the output layer of the embedder neural network. That is, the first output can be forced to have a desired format, size, or dimensionality by adding or removing neurons or other internal parameters to or from the output layer of the embedder neural network. Accordingly, the first output can be forced to have a smaller (e.g., in some cases, many orders of magnitude smaller) format, size, or dimensionality than the selected data candidate. Accordingly, the first output can be considered as an embedding (e.g., a latent vector representation) that the embedder neural network has predicted or inferred corresponds to the selected data candidate.

Furthermore, note that, if the embedder neural network has so far undergone no or little training, then the first output can be highly inaccurate (e.g., the first output can fail to be a correct or proper embedding of the selected data candidate).

In various aspects, the training component can execute the another deep learning neural network on the first output, and such execution can cause the another deep learning neural network to produce a second output. More specifically, the training component can feed the first output to an input layer of the another deep learning neural network, the first output can complete a forward pass through one or more hidden layers of the another deep learning neural network, and an output layer of the another deep learning neural network can compute or calculate the second output based on activations produced by the one or more hidden layers of the another deep learning neural network.

Note that, as above, the format, size, or dimensionality of the second output can be controlled or otherwise determined by the number or arrangement of neurons (or by the number or arrangement of other internal parameters, such as convolutional kernels) that are in the output layer of the another deep learning neural network. That is, the second output can be forced to have a desired format, size, or dimensionality by adding or removing neurons or other internal parameters to or from the output layer of the another deep learning neural network. So, the second output can be forced to have a same format, size, or dimensionality as the selected data candidate. Accordingly, the second output can be considered as an approximation or recreation of the selected data candidate, as predicted or inferred by the another deep learning neural network.

Also as above, note that, if the another deep learning neural network has so far undergone no or little training, then the second output can be highly inaccurate (e.g., the second output can be very different from the selected data candidate).

In various aspects, the training component can compute an error or loss (e.g., MAE, MSE, cross-entropy) between the second output and the selected data candidate. In various instances, the training component can incrementally update the trainable internal parameters of both the embedder neural network and the another deep learning neural network, by performing backpropagation (e.g., stochastic gradient descent) driven by the computed error or loss. In other words, the embedder neural network and the another deep learning neural network can be considered as collectively forming an encoder-decoder deep learning pipeline, where the embedder neural network can be considered as the encoder, and where the another deep learning neural network can be considered as the decoder.

In various cases, the training component can repeat this training procedure for any suitable number of data candidates. Such training can ultimately cause the trainable internal parameters of the embedder neural network to become iteratively optimized for accurately generating embeddings based on inputted data candidates, and such training can also ultimately cause the trainable internal parameters of the another deep learning neural network to become iteratively optimized for accurately recreating data candidates based on inputted embeddings. In various aspects, the training component can implement any suitable training batch sizes, any suitable training termination criterion, or any suitable error, loss, or objective function.

Note that any entity or third-party that lacks the another deep learning neural network can be considered as being unable to decode embeddings that are generated by the embedder neural network. So, the embeddings generated by the embedder neural network can thus be considered as privacy-preserving.

Various embodiments described herein can be employed to use hardware or software to solve problems that are highly technical in nature (e.g., to facilitate data candidate querying via embeddings for deep learning refinement), that are not abstract and that cannot be performed as a set of mental acts by a human. Further, some of the processes performed can be performed by a specialized computer (e.g., a deep learning neural network having internal parameters such as convolutional kernels) for carrying out defined acts related to deep learning.

For example, such defined acts can include: accessing, by a device operatively coupled to a processor, a test data candidate provided by a client; generating, by the device and via a first deep learning neural network, an inferencing output based on the test data candidate; generating, by the device and via at least one second deep learning neural network, at least one embedding based on the test data candidate; accessing, by the device, feedback indicating whether the client accepts or rejects the inferencing output; identifying, by the device, in response to the feedback indicating that the client rejects the inferencing output, and in a candidate-embedding dataset, one or more annotated data candidates whose embeddings are within a threshold level of similarity to the at least one embedding; and retraining, by the device, the first deep learning neural network based on the one or more annotated data candidates.

Such defined acts are not performed manually by humans. Indeed, neither the human mind nor a human with pen and paper can electronically access a data candidate, electronically generate an embedding (e.g., latent vector) of that data candidate via a deep learning neural network, electronically identify substantively-similar data candidates based on that embedding, and electronically retrain another deep learning neural network using those substantively-similar data candidates. Indeed, a deep learning neural network is an inherently-computerized construct that simply cannot be meaningfully executed or trained in any way by the human mind without computers. Furthermore, deep learning embeddings are latent vector representations of electronic data that also cannot be meaningfully implemented in any way by the human mind with computers. Accordingly, a computerized tool that can retrain a deep learning neural network by leveraging deep learning embeddings to identify substantively-similar data candidates is likewise inherently-computerized and cannot be implemented in any sensible, practical, or reasonable way without computers.

Moreover, various embodiments described herein can integrate into a practical application various teachings relating to data candidate querying via embeddings for deep learning refinement. As explained above, when a deep learning neural network fails to accurately analyze a given data candidate, it can be desired to retrain the deep learning neural network on other data candidates that are substantively-similar to that given data candidate. Oftentimes, the given data candidate can be no longer available for retraining, such as due to privacy concerns or regulations. In such case, substantively-similar data candidates cannot be identified for retraining, which is undesirable. Even if the given data candidate is available, existing techniques for identifying substantively-similar data candidates for retraining rely upon manual data selection by subject matter experts. Such manual selection is excessively time-consuming and error-prone, which is undesirable.

Various embodiments described herein can address one or more of these technical problems. Specifically, various embodiments described herein can utilize deep learning embeddings (e.g., latent vectors) to identify substantively-similar data candidates for retraining. In particular, an embedder neural network can be trained in unsupervised fashion as described herein. In various aspects, the embedder neural network can generate embeddings for inputted data candidates. Accordingly, when given a lake or store of data candidates, the embedder neural network can generate a respective embedding for each data candidate in the lake/store. Moreover, when given any data candidate that a deep learning neural network has failed to properly analyze, the embedder neural network can generate an embedding for that given data candidate, and such embedding can be leveraged to find substantively-similar data candidates in the lake/store (e.g., embeddings can be compared with cosine similarity or Euclidean distance). Once such substantively-similar data candidates are found, the deep learning neural network can be retrained accordingly. Note that such embodiments do not rely upon manual comparison between data candidates. Furthermore, note that such embodiments can be implemented, even if the given data candidate is no longer available due to privacy restrictions (e.g., the embedding can be considered as a compressed, jumbled, encrypted, or otherwise privacy-preserving representation of that given data candidate, such that storage, distribution, or utilization of the embedding does not invoke privacy concerns). In stark contrast, existing techniques rely upon manual comparison between data candidates and cannot be utilized when the given data candidate is no longer available. In this way, various embodiments described herein can be considered as an improved technique for facilitating ongoing refinement of deep learning neural networks (e.g., for identifying new data that is substantively-similar to failure data, so that the deep learning neural network can be retrained appropriately).

Furthermore, as mentioned above, some embodiments described herein can utilize deep learning embeddings to streamline annotation procedures. As mentioned above, when given a lake or store of data candidates, the embedder neural network can generate a respective embedding for each data candidate in the lake/store. Moreover, when given any data candidate that already has a ground-truth annotation, the embedder neural network can generate an embedding for that given data candidate, and such embedding can be leveraged to find substantively-similar data candidates in the lake/store (e.g., embeddings can be compared with cosine similarity or Euclidean distance). Once such substantively-similar data candidates are found, they can be given the same or similar annotations as the given data candidate. Accordingly, deep learning embeddings as described herein can be considered as increasing case of annotation.

For at least these reasons, various embodiments described herein certainly constitute concrete and tangible technical improvements in the field of deep learning, and such embodiments therefore clearly qualify as useful and practical applications of computers.

Furthermore, various embodiments described herein can control real-world tangible devices based on the disclosed teachings. For example, various embodiments described herein can electronically execute or train real-world deep learning neural networks.

It should be appreciated that the herein figures and description provide non-limiting examples of various embodiments and are not necessarily drawn to scale.

FIG. 1 illustrates a block diagram of an example, non-limiting system 100 that can facilitate annotated data candidate querying via embeddings for deep learning refinement in accordance with one or more embodiments described herein. As shown, an embedding query system 102 can be electronically integrated, via any suitable wired or wireless electronic connections, with a deep learning neural network 104 or with a test data candidate 106.

In various embodiments, the deep learning neural network 104 can be any suitable artificial neural network that can have or otherwise exhibit any suitable internal architecture. For instance, the deep learning neural network 104 can have an input layer, one or more hidden layers, and an output layer. In various instances, any of such layers can be coupled together by any suitable interneuron connections or inter-layer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

Regardless of its internal architecture, the deep learning neural network 104 can be configured to perform an inferencing task on data candidates. In various aspects, a data candidate can be any suitable electronic data having any suitable format, size, or dimensionality. In other words, a data candidate can be one or more scalars, one or more vectors, one or more matrices, one or more tensors, one or more character strings, or any suitable combination thereof. As a non-limiting example, a data candidate can be one or more two-dimensional images (e.g., one or more pixel arrays). As another non-limiting example, a data candidate can be one or more three-dimensional images (e.g., one or more voxel arrays). As yet another non-limiting example, a data candidate can be one or more electronic audio files (e.g., one or more timeseries of pressure values or decibel values). As still another non-limiting example, a data candidate can be waveform-spectra (e.g., data represented in a frequency-domain instead of a time-domain). As even another non-limiting example, a data candidate can be an electronic textual file (e.g., one or more strings of text). As another non-limiting example, a data candidate can be any suitable combination thereof.

In various instances, the inferencing task can be or otherwise involve computational generation of any suitable prediction or forecast for or with respect to a data candidate. As a non-limiting example, the inferencing task can be classification. In such case, the deep learning neural network 104 can be configured to receive a particular data candidate as input and to produce as output a classification label for that particular data candidate. As another non-limiting example, the inferencing task can be segmentation. In such case, the deep learning neural network 104 can be configured to receive a particular data candidate as input and to produce as output a segmentation mask for that particular data candidate. As even another non-limiting example, the inferencing task can be regression. In such case, the deep learning neural network 104 can be configured to receive a particular data candidate as input and to produce as output a regression result for (e.g., a denoised version of, a resolution-enhanced version of, a continuously-variable scalar for) that particular data candidate. As yet another non-limiting example, the inferencing task can be any suitable combination of classification, segmentation, or regression.

In any case, the deep learning neural network 104 can have been trained in any suitable fashion to perform the inferencing task. Indeed, in various aspects, the deep learning neural network 104 can have been trained in supervised fashion on annotated data candidates to perform the inferencing task. Such training can have involved any suitable error or objective function (e.g., cross-entropy), any suitable optimization algorithm (e.g., stochastic gradient descent), any suitable number of training epochs, or any suitable training batch sizes. However, this is a mere non-limiting example. In other cases, the deep learning neural network 104 can have been trained to perform the inferencing task in unsupervised fashion or in reinforcement learning fashion.

After having been trained, the deep learning neural network 104 can be deployed or otherwise implemented in any suitable operational context. As a non-limiting example, the deep learning neural network 104 can be deployed in a medical or clinical operational context. In such cases, a data candidate can be a medical image (e.g., a computed tomography (CT) scanned image, a magnetic resonance imaging (MRI) scanned image, a positron emission tomography (PET) scanned image, an X-ray scanned image, an ultrasound scanned image) that depicts any suitable anatomical structure (e.g., tissue, organ, body part, or portion thereof) of a medical patient (e.g., human, animal, or otherwise), and the inferencing task can be any suitable classification, segmentation, or regression that can be leveraged for diagnostic or prognostic purposes. Accordingly, the deep learning neural network 104 can, in such embodiments, be hosted on any suitable medical imaging or scanning device (e.g., can be hosted on a CT scanner, on an MRI scanner, on a PET scanner, on an X-ray scanner, on an ultrasound scanner).

In various embodiments, the test data candidate 106 can be any suitable data candidate on which it is desired to perform the inferencing task (e.g., on which it is desired to execute the deep learning neural network 104). In various aspects, the test data candidate 106 can be provided in any suitable fashion by any suitable client (not shown), whether human or otherwise. In some instances, the client can provide the test data candidate 106 via any suitable human-computer interface device (not shown). As some non-limiting examples, the human-computer interface device can be a keyboard, a keypad, a touchscreen, a computer mouse, or a voice-control system. In various cases, the test data candidate 106 can be subject to privacy restrictions which limit for how long the test data candidate 106 can be electronically stored, electronically read/viewed, or otherwise electronically manipulated. Accordingly, it can be the case that the test data candidate 106 is available for performance of the inferencing task only during a short, limited, or otherwise temporary time period.

In various cases, it might be determined after that short, limited, or temporary time period that the deep learning neural network 104 is not able to accurately perform the inferencing task on the test data candidate 106. So, it can be desired to retrain or refine the deep learning neural network

104 using data that is substantively-similar to the test data candidate 106. As described herein, the embedding query system 102 can facilitate such retraining or refinement, notwithstanding that the test data candidate 106 might no longer be available.

In various embodiments, the embedding query system 102 can comprise a processor 108 (e.g., computer processing unit, microprocessor) and a non-transitory computer-readable memory 110 that is operably or operatively or communicatively connected or coupled to the processor 108. The non-transitory computer-readable memory 110 can store computer-executable instructions which, upon execution by the processor 108, can cause the processor 108 or other components of the embedding query system 102 (e.g., access component 112, model component 114, embedding component 116, feedback component 118, search component 120, update component 122) to perform one or more acts. In various embodiments, the non-transitory computer-readable memory 110 can store computer-executable components (e.g., access component 112, model component 114, embedding component 116, feedback component 118, search component 120, update component 122), and the processor 108 can execute the computer-executable components.

In various embodiments, the embedding query system 102 can comprise an access component 112. In various aspects, the access component 112 can electronically receive or otherwise electronically access the deep learning neural network 104 or the test data candidate 106. In various instances, the access component 112 can electronically retrieve the deep learning neural network 104 or the test data candidate 106 from any suitable centralized or decentralized data structures (not shown) or from any suitable centralized or decentralized computing devices (not shown). In any case, the access component 112 can electronically obtain or access the deep learning neural network 104 or the test data candidate 106, such that other components of the embedding query system 102 can electronically interact with the deep learning neural network 104 or with the test data candidate 106.

In various embodiments, the embedding query system 102 can comprise a model component 114. In various aspects, as described herein, the model component 114 can execute (e.g., during the short, limited, or temporary time period in which the test data candidate 106 is available) the deep learning neural network 104 on the test data candidate 106, thereby yielding an inferencing output.

In various embodiments, the embedding query system 102 can comprise an embedding component 116. In various instances, as described herein, the embedding component 116 can execute (e.g., also during the short, limited, or temporary time period in which the test data candidate 106 is available) an embedder neural network on the test data candidate 106, thereby yielding an embedding.

In various embodiments, the embedding query system 102 can comprise a feedback component 118. In various cases, as described herein, the feedback component 118 can receive (e.g., during or after the short, limited, or temporary time period in which the test data candidate 106 is available) feedback indicating whether the client approves or disapproves the inferencing output.

In various embodiments, the embedding query system 102 can comprise a search component 120. In various aspects, as described herein, the search component 120 can, in response to the feedback indicating disapproval of the inferencing output, query (e.g., after the short, limited, or temporary time period in which the test data candidate 106 is available) a candidate-embedding dataset for annotated data candidates having embeddings that are similar to the embedding of the test data candidate 106.

In various embodiments, the embedding query system 102 can comprise an update component 122. In various instances, as described herein, the update component 122 can retrain (e.g., after the short, limited, or temporary time period in which the test data candidate 106 is available) the deep learning neural network 104 on the annotated data candidates identified by the search component 120.

Figure 2:
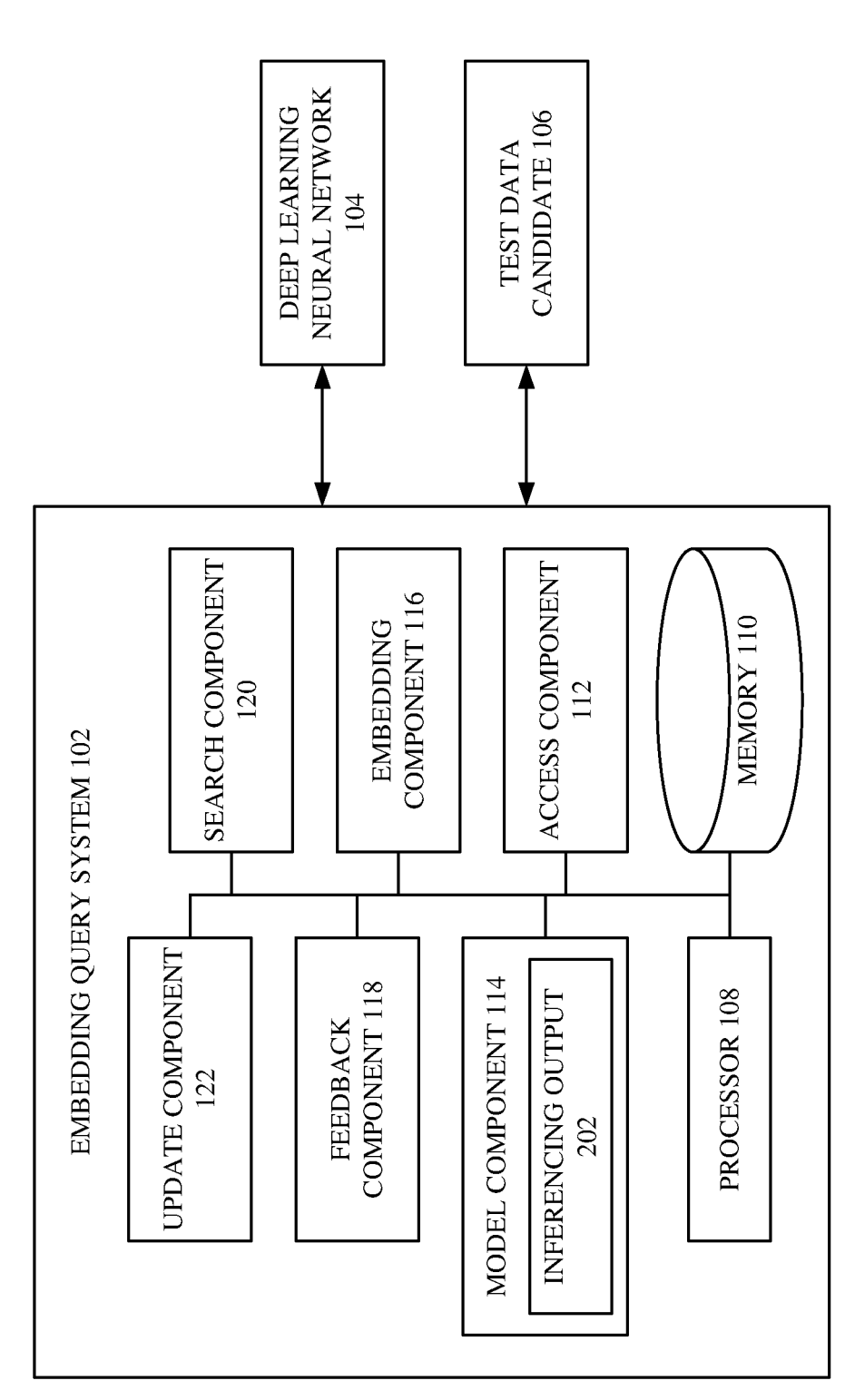
FIG. 2 illustrates a block diagram of an example, non-limiting system including an inferencing output that facilitates data candidate querying via embeddings for deep learning refinement in accordance with one or more embodiments described herein.

FIG. 2 illustrates a block diagram of an example, non-limiting system 200 including an inferencing output that can facilitate data candidate querying via embeddings for deep learning refinement in accordance with one or more embodiments described herein. As shown, the system 200 can, in some cases, comprise the same components as the system 100, and can further comprise an inferencing output 202.

In various embodiments, the model component 114 can electronically generate the inferencing output 202, by executing the deep learning neural network 104 on the test data candidate 106. Non-limiting aspects are described with respect to FIG. 3.

Figure 3:
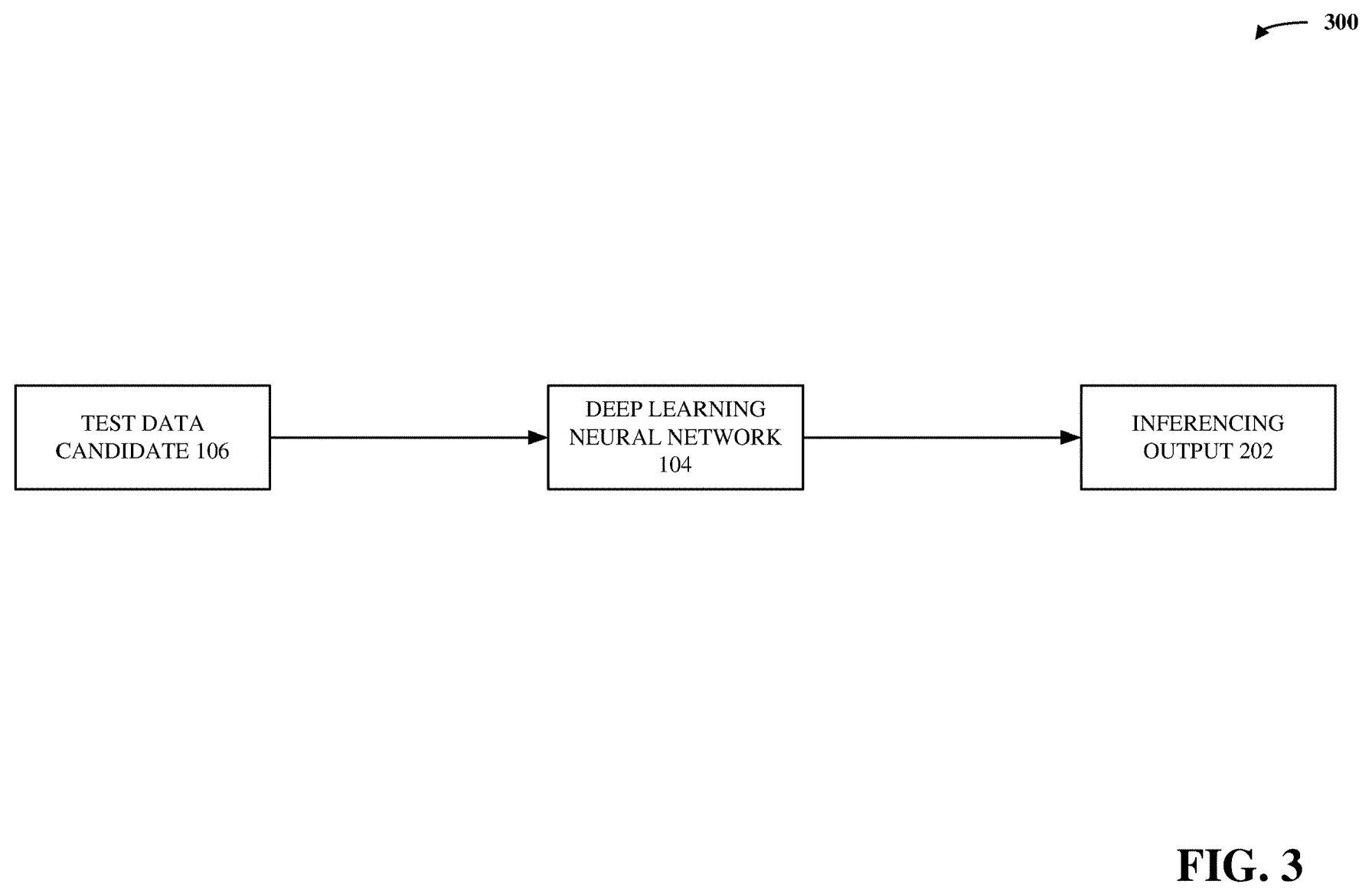

FIG. 3 illustrates an example, non-limiting block diagram 300 showing how the inferencing output 202 can be obtained in accordance with one or more embodiments described herein.

In various aspects, the model component 114 can electronically control or otherwise electronically operate the deep learning neural network 104. Accordingly, in various instances, the model component 114 can electronically execute the deep learning neural network 104 on the test data candidate 106. In various cases, such execution can cause the deep learning neural network 104 to produce the inferencing output 202. More specifically, the model component 114 can feed the test data candidate 106 to an input layer of the deep learning neural network 104. In various aspects, the test data candidate 106 can complete a forward pass through one or more hidden layers of the deep learning neural network 104. In various instances, an output layer of the deep learning neural network 104 can compute or otherwise calculate the inferencing output 202 based on activation maps generated by the one or more hidden layers of the deep learning neural network 104.

In any case, the inferencing output 202 can be considered as the predicted computational result that the deep learning neural network 104 has determined corresponds to the test data candidate 106. Accordingly, the inferencing output 202 can be any suitable electronic data whose format, size, or dimensionality can depend upon the inferencing task that the deep learning neural network 104 is configured or trained to perform. As a non-limiting example, suppose that the inferencing task is classification. In such case, the inferencing output 202 can be a classification label that the deep learning neural network 104 believes or infers corresponds to that the test data candidate 106. As another non-limiting example, suppose that the inferencing task is segmentation. In such case, the inferencing output 202 can be a segmentation mask that the deep learning neural network 104 believes or infers corresponds to that the test data candidate 106. As yet another non-limiting example, suppose that the inferencing task is regression. In such case, the inferencing output 202 can be a regression result (e.g., one or more continuously variable scalars, vectors, matrices, or tensors) that the deep learning neural network 104 believes or infers corresponds to that the test data candidate 106.

Note that the model component 114 can generate the inferencing output 202 during the short, limited, or temporary time period in which the test data candidate 106 is available.

Figure 4:
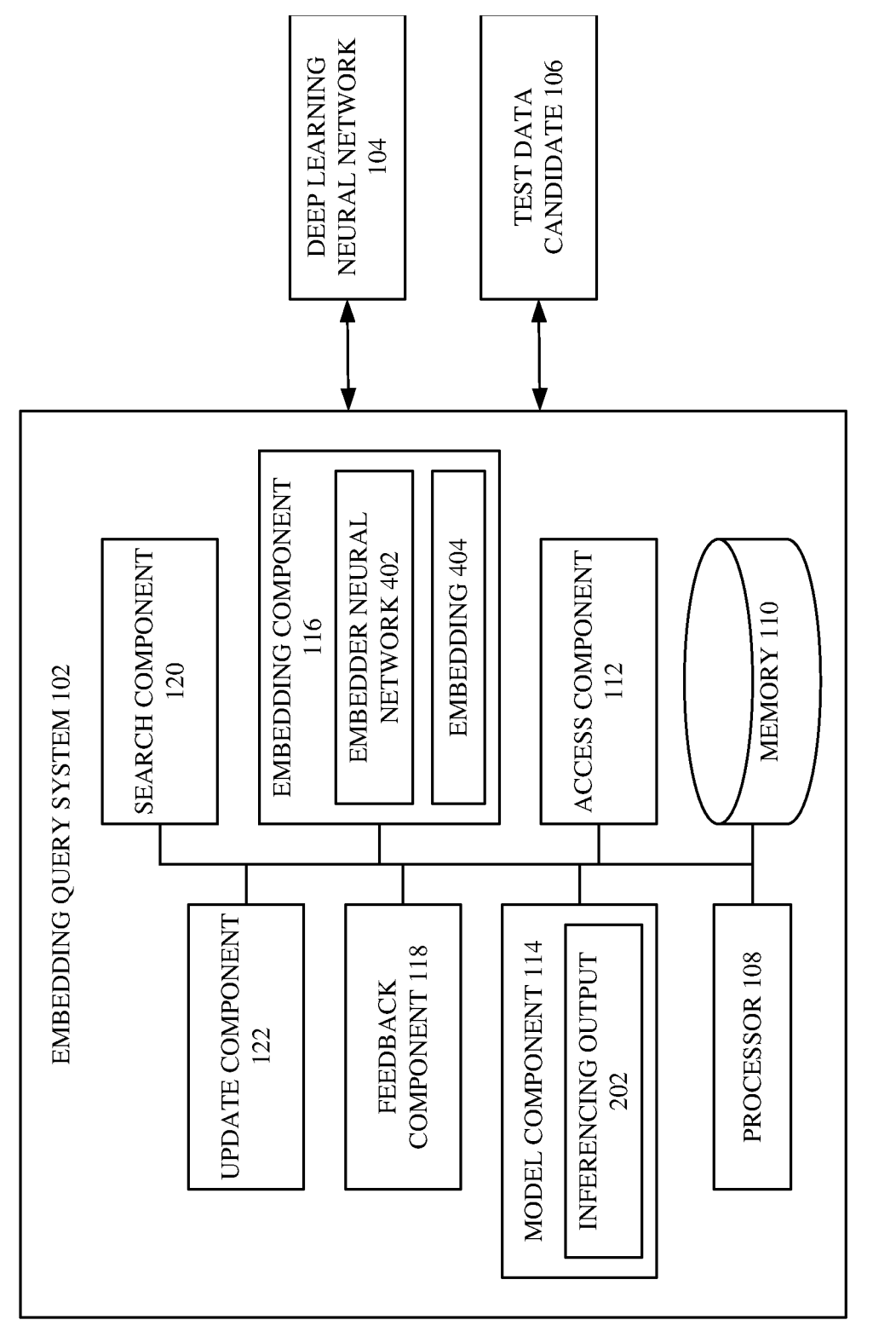
FIG. 4 illustrates a block diagram of an example, non-limiting system including an embedder neural network and an embedding that facilitates data candidate querying via embeddings for deep learning refinement in accordance with one or more embodiments described herein.

FIG. 4 illustrates a block diagram of an example, non-limiting system 400 including an embedder neural network and an embedding that can facilitate data candidate querying via embeddings for deep learning refinement in accordance with one or more embodiments described herein. As shown, the system 400 can, in some cases, comprise the same components as the system 200, and can further comprise an embedder neural network 402 or an embedding 404.

In various aspects, the embedder neural network 402 can be any suitable artificial neural network that can have or otherwise exhibit any suitable internal architecture. For instance, the embedder neural network 402 can have an input layer, one or more hidden layers, and an output layer. In various instances, any of such layers can be coupled together by any suitable interneuron connections or inter-layer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

Regardless of its internal architecture, the embedder neural network 402 can be configured, as described herein, to generate embeddings of inputted data candidates. Accordingly, the embedding component 116 can electronically generate the embedding 404, by executing the embedder neural network 402 on the test data candidate 106. Non-limiting aspects are described with respect to FIG. 5.

Figure 5:
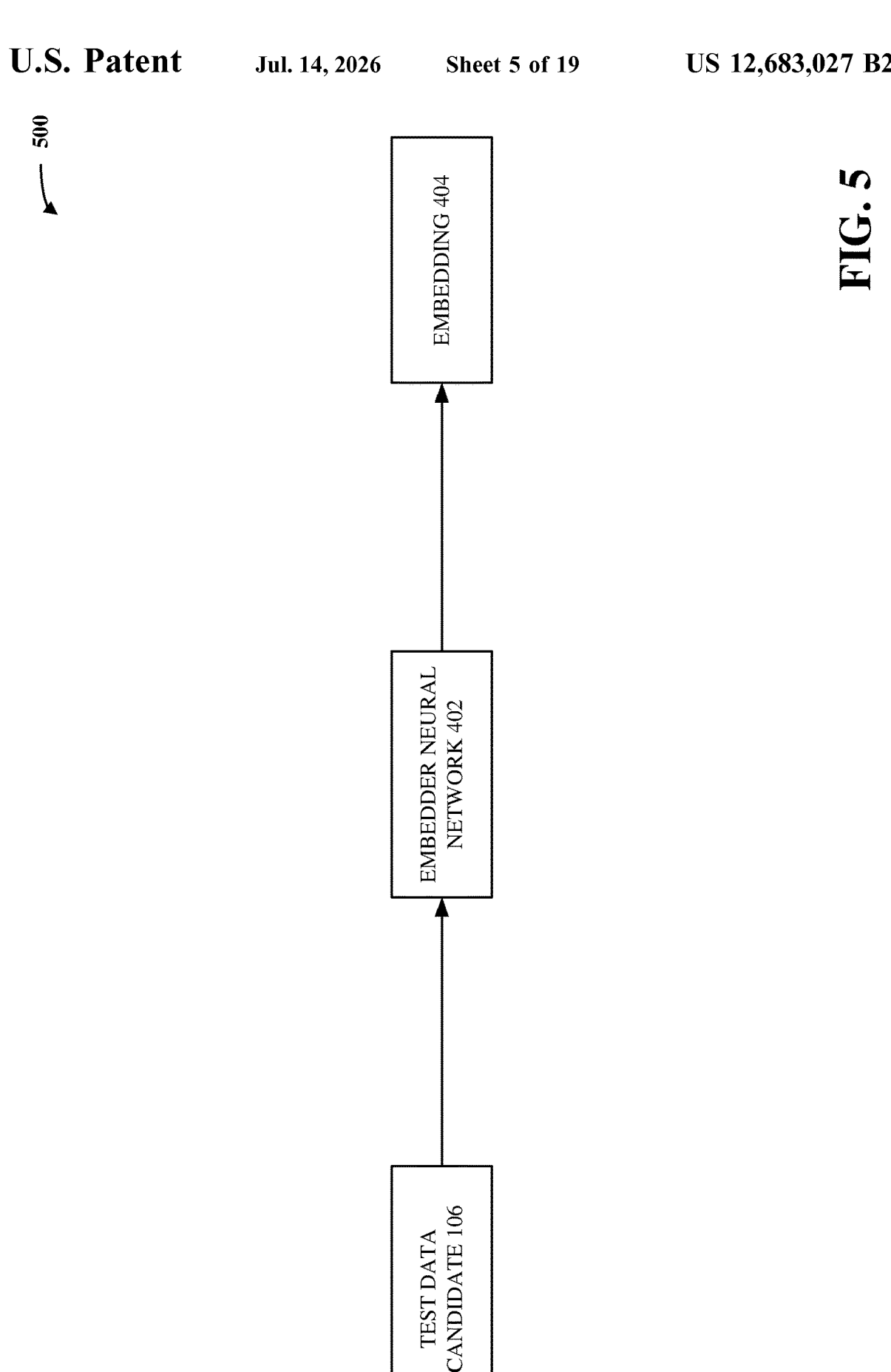
FIG. 5 illustrates an example, non-limiting block diagram showing how an embedder neural network can generate an embedding for a test data candidate in accordance with one or more embodiments described herein.

FIG. 5 illustrates an example, non-limiting block diagram 500 showing how the embedder neural network 402 can generate the embedding 404 in accordance with one or more embodiments described herein.

In various aspects, the embedding component 116 can electronically control or otherwise electronically operate the embedder neural network 402. Accordingly, in various instances, the embedding component 116 can electronically execute the embedder neural network 402 on the test data candidate 106. In various cases, such execution can cause the embedder neural network 402 to produce the embedding 404. In particular, the embedding component 116 can feed the test data candidate 106 to an input layer of the embedder neural network 402. In various aspects, the test data candidate 106 can complete a forward pass through one or more hidden layers of the embedder neural network 402. In various instances, an output layer of the embedder neural network 402 can compute or otherwise calculate the embedding 404 based on activation maps generated by the one or more hidden layers of the embedder neural network 402.

In any case, the embedding 404 can be considered as a latent vector representation that the embedder neural network 402 believes or infers corresponds to the test data candidate 106. More specifically, the embedding 404 can be one or more scalars, one or more vectors, one or more matrices, one or more tensors, or any suitable combination thereof. In various aspects, the dimensionality of the embedding 404 (e.g., the total number of numerical elements within the embedding 404) can be smaller (e.g., many orders of magnitude smaller, in some cases) than the dimensionality of the test data candidate 106. In various instances, despite its smaller dimensionality, the embedding 404 can nevertheless be considered as representing, albeit in hidden or non-apparent fashion, at least some substantive content of the test data candidate 106.

As a non-limiting example, suppose that the test data candidate 106 is an image having hundreds of thousands of pixels. In such case, the embedding 404 can be a vector having merely tens or dozens of scalar elements. Despite its significantly smaller dimensionality, such vector can nevertheless encode or represent at least some substantive aspect of whatever is visually illustrated in the image. For instance, if the image depicts a lung of a medical patient, then the tens or dozens of scalar elements of the vector can have particular values. However, if the image instead depicts a brain of a medical patient, the tens or dozens of scalar elements of the vector can instead have different values. Moreover, a third-party that has no connection to the embedder neural network 402 can be unable to recreate the image from that vector alone (e.g., the third-party would not be able to know that the image depicts a lung or a brain merely from considering the vector in isolation).

Accordingly, the embedding 404 can, in some aspects, be considered as a compressed and encrypted version of the test data candidate 106.

Note that the embedding component 116 can generate the embedding 404 during the short, limited, or temporary time period in which the test data candidate 106 is available.

Figure 6:
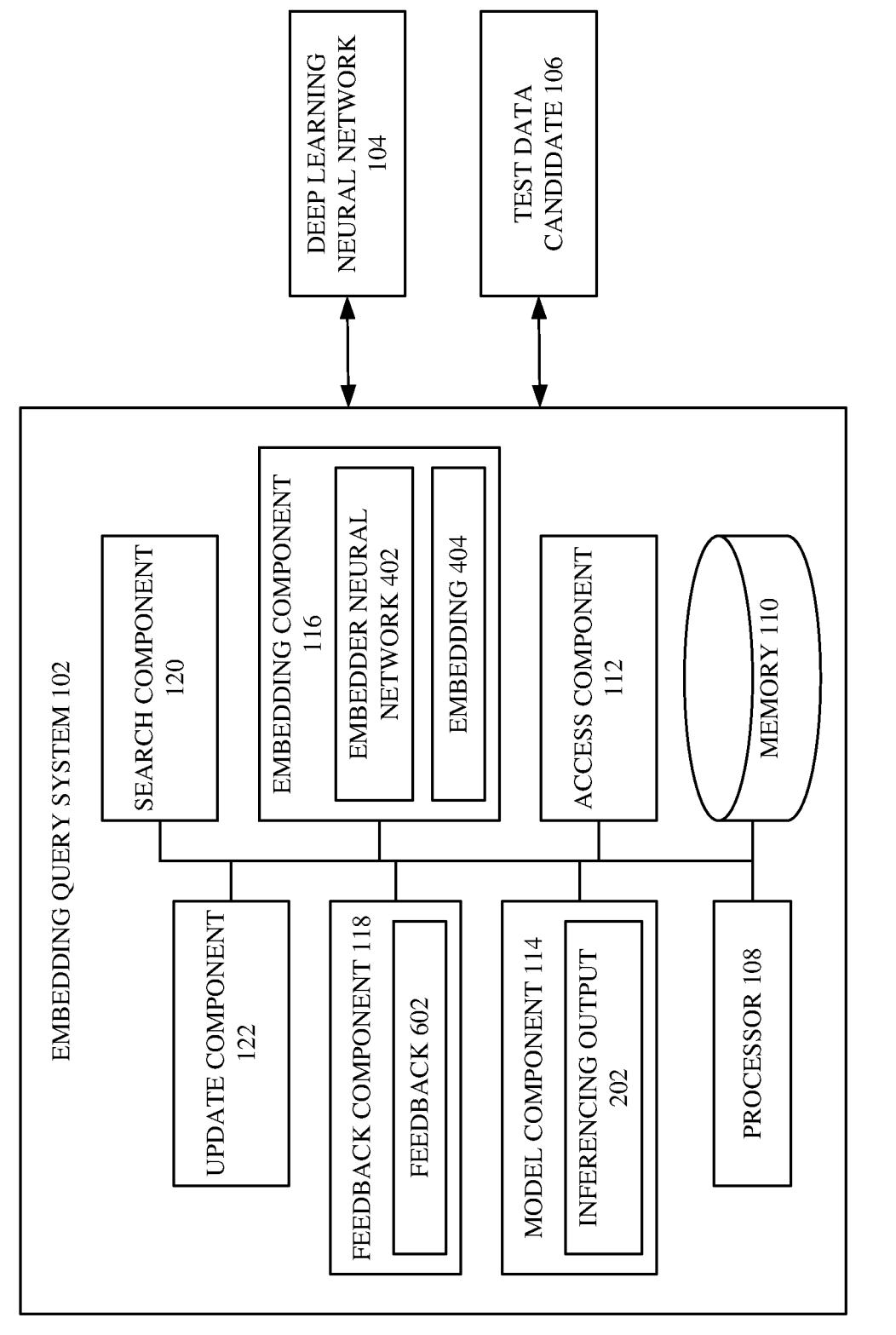
FIG. 6 illustrates a block diagram of an example, non-limiting system including feedback that facilitates data candidate querying via embeddings for deep learning refinement in accordance with one or more embodiments described herein.

FIG. 6 illustrates a block diagram of an example, non-limiting system 600 including feedback that can facilitate data candidate querying via embeddings for deep learning refinement in accordance with one or more embodiments described herein. As shown, the system 600 can, in some cases, comprise the same components as the system 400, and can further comprise feedback 602.

In various embodiments, the feedback component 118 can electronically receive, electronically retrieve, electronically obtain, or otherwise electronically access the feedback 602. In various aspects, the feedback 602 can be any suitable electronic data having any suitable format, size, or dimensionality. In various instances, the feedback 602 can indicate or otherwise convey approval (e.g., acceptance) or disapproval (e.g., rejection) of the inferencing output 202. More specifically, the feedback 602 can be provided by the client that supplied the test data candidate 106 (e.g., the client can provide the feedback 602 via any suitable human-computer interface device such as a keyboard, keypad, or touchscreen). In various aspects, the feedback 602 can indicate or convey that the client has approved or accepted the inferencing output 202. In such case, this can be interpreted to mean that the client believes that the inferencing output 202 is correct (e.g., believes that the deep learning neural network 104 accurately performed the inferencing task on the test data candidate 106). In other aspects, the feedback 602 can instead indicate or convey that the client has disapproved or rejected the inferencing output 202. In such case, this can be interpreted to mean that the client believes that the inferencing output 202 is incorrect (e.g., believes that the deep learning neural network 104 inaccurately performed the inferencing task on the test data candidate 106).

Note that the feedback component 118 can access the feedback 602 during or after the short, limited, or temporary time period in which the test data candidate 106 is available.

Figure 7:
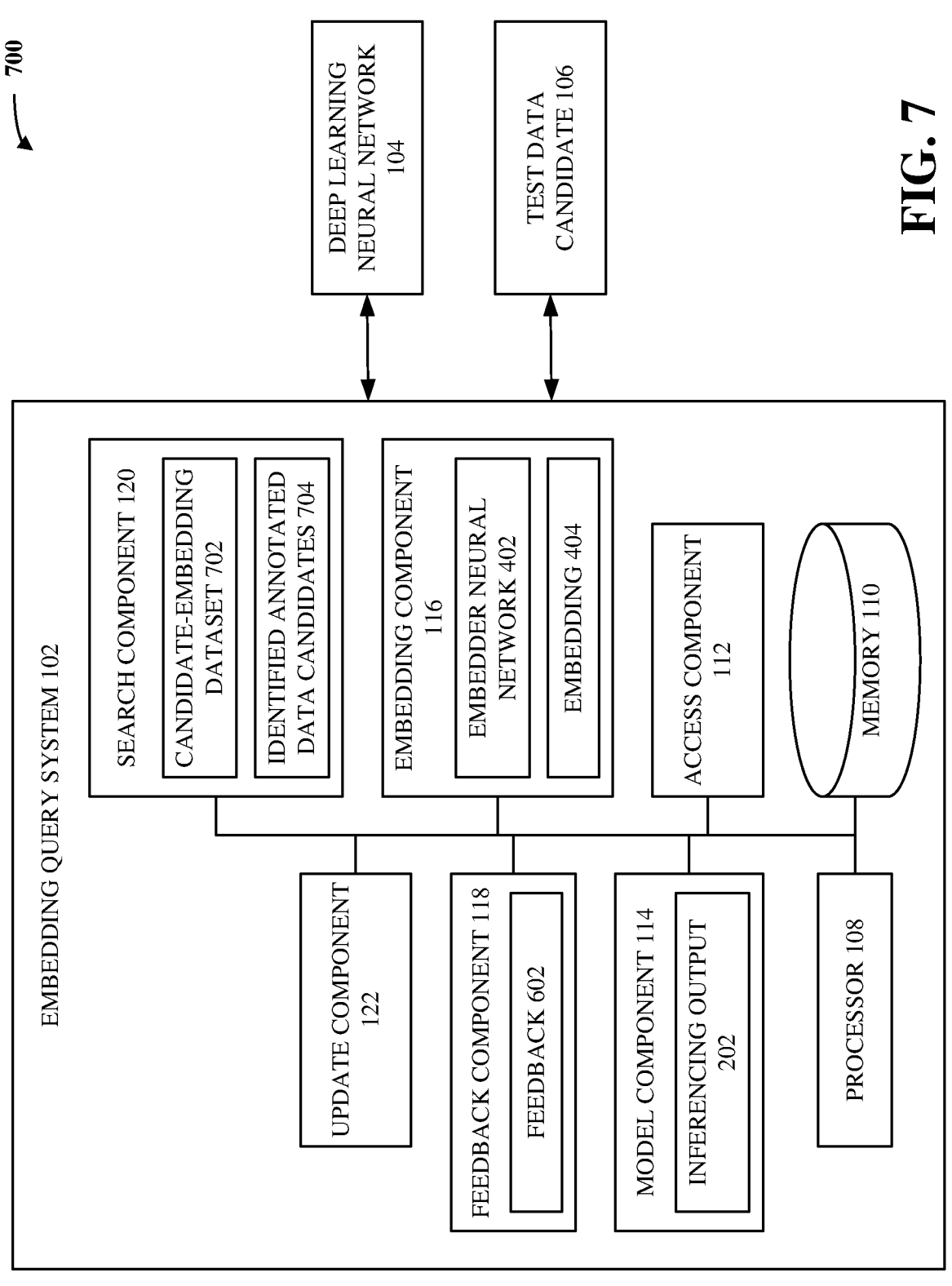
FIG. 7 illustrates a block diagram of an example, non-limiting system including a candidate-embedding dataset that facilitates data candidate querying via embeddings for deep learning refinement in accordance with one or more embodiments described herein.

FIG. 7 illustrates a block diagram of an example, non-limiting system 700 including a candidate-embedding dataset that can facilitate data candidate querying via embeddings for deep learning refinement in accordance with one or more embodiments described herein. As shown, the system 700 can, in some cases, comprise the same components as the system 600, and can further comprise a candidate-embedding dataset 702 or a set of identified annotated data candidates 704.

In various aspects, the search component 120 can electronically store, electronically maintain, electronically control, or otherwise electronically access the candidate-embedding dataset 702. In various instances, the candidate-embedding dataset 702 can map, link, or otherwise correlate various data candidates (e.g., both annotated and unannotated) to respective embeddings (e.g., such embeddings can have been generated by the embedder neural network 402). In various cases, it is possible that the feedback 602 indicates disapproval or rejection of the inferencing output 202. In response to such indication, the search component 120 can query the candidate-embedding dataset 702 for one or more annotated data candidates whose embeddings match or are otherwise similar to the embedding 404. Such one or more annotated data candidates can be referred to as the set of identified annotated data candidates 704. Various non-limiting aspects are described with respect to FIGS. 8-9.

Figure 8:
FIG. 8 illustrates an example, non-limiting block diagram showing a candidate-embedding dataset in accordance with one or more embodiments described herein.

First, consider FIG. 8. FIG. 8 illustrates an example, non-limiting block diagram 800 of the candidate-embedding dataset 702 in accordance with one or more embodiments described herein.

As shown, the candidate-embedding dataset 702 can comprise a set of annotated data candidates 802. In various aspects, the set of annotated data candidates 802 can comprise n data candidates for any suitable positive integer n: an annotated data candidate 802(1) to an annotated data candidate 802(n). In various instances, each of the set of annotated data candidates 802 can be any suitable data candidate having the same format, size, or dimensionality as the test data candidate 106 and for which a respective ground-truth annotation with respect to the inferencing task performable by the deep learning neural network 104 is known or otherwise available.

As also shown, the candidate-embedding dataset 702 can comprise a set of unannotated data candidates 806. In various aspects, the set of unannotated data candidates 806 can comprise m data candidates for any suitable positive integer m: an unannotated data candidate 806(1) to an unannotated data candidate 806(m). In various instances, each of the set of unannotated data candidates 806 can be any suitable data candidate having the same format, size, or dimensionality as the test data candidate 106 but for which a respective ground-truth annotation with respect to the inferencing task performable by the deep learning neural network 104 is unknown or otherwise unavailable.

In various cases, the candidate-embedding dataset 702 can comprise a set of embeddings 804 that respectively correspond (e.g., in one-to-one fashion) to the set of annotated data candidates 802. Accordingly, since the set of annotated data candidates 802 can comprise n data candidates, the set of embeddings 804 can comprise n embeddings: an embedding 804(1) to an embedding 804(n). In various aspects, each of the set of embeddings 804 can be a latent vector representation of a respective one of the set of annotated data candidates 802. Accordingly, each of the set of embeddings 804 can be or can have been obtained by executing the embedder neural network 402 on a respective one of the set of annotated data candidates 802. As a non-limiting example, the annotated data candidate 802(1) can correspond to the embedding 804(1). Thus, the embedding 804(1) can be considered as a latent vector representing at least some substantive content of the annotated data candidate 802(1). In various cases, the embedder neural network 402 can have been executed on the annotated data candidate 802(1), and such execution can have caused the embedder neural network 402 to produce as output the embedding 804(1). As another non-limiting example, the annotated data candidate 802(n) can correspond to the embedding 804(n). So, the embedding 804(n) can be considered as a latent vector representing at least some substantive content of the annotated data candidate 802(n). Just as above, the embedder neural network 402 can have been executed on the annotated data candidate 802(n), and such execution can have caused the embedder neural network 402 to produce as output the embedding 804(n).

In various instances, the candidate-embedding dataset 702 can comprise a set of embeddings 808 that respectively correspond (e.g., in one-to-one fashion) to the set of unannotated data candidates 806. Accordingly, since the set of unannotated data candidates 806 can comprise m data candidates, the set of embeddings 808 can comprise m embeddings: an embedding 808(1) to an embedding 808(m). In various cases, each of the set of embeddings 808 can be a latent vector representation of a respective one of the set of unannotated data candidates 806. Accordingly, each of the set of embeddings 808 can be or can have been obtained by executing the embedder neural network 402 on a respective one of the set of unannotated data candidates 806. As a non-limiting example, the unannotated data candidate 806(1) can correspond to the embedding 808(1). So, the embedding 808(1) can be considered as a latent vector representing at least some substantive content of the unannotated data candidate 806(1). In various aspects, the embedder neural network 402 can have been executed on the unannotated data candidate 806(1), and such execution can have caused the embedder neural network 402 to produce as output the embedding 808(1). As another non-limiting example, the unannotated data candidate 806(m) can correspond to the embedding 808(m). Thus, the embedding 808(m) can be considered as a latent vector representing at least some substantive content of the unannotated data candidate 806(m). Just as above, the embedder neural network 402 can have been executed on the unannotated data candidate 806(m), and such execution can have caused the embedder neural network 402 to produce as output the embedding 808(m).

Figure 9:
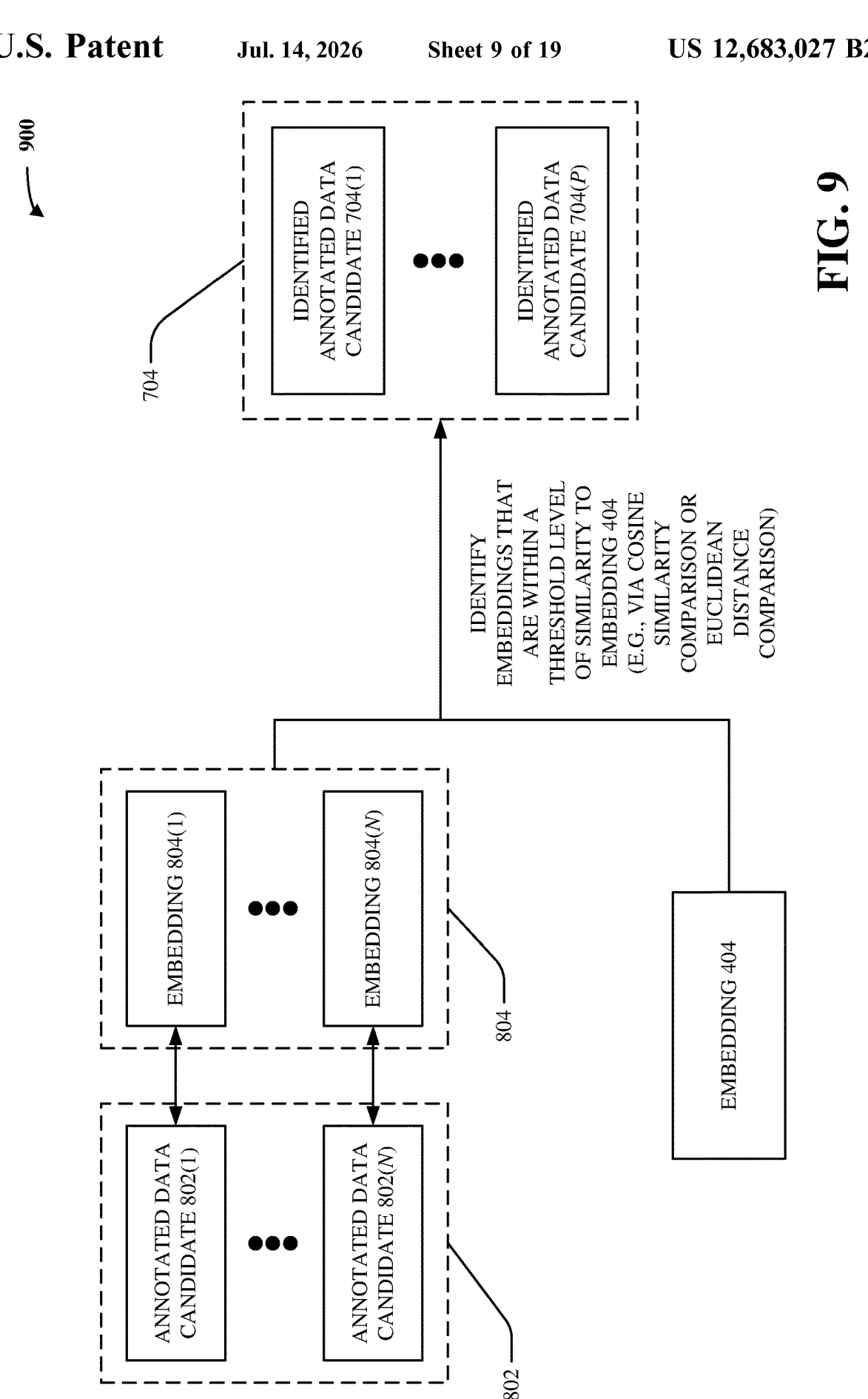
FIG. 9 illustrates an example, non-limiting block diagram showing how a candidate-embedding dataset can be queried for annotated data candidates in accordance with one or more embodiments described herein.

Now, consider FIG. 9. FIG. 9 illustrates an example, non-limiting block diagram 900 showing how the candidate-embedding dataset 702 can be queried for annotated data candidates in accordance with one or more embodiments described herein.

In various aspects, as mentioned above, the feedback 602 can indicate disapproval or rejection of the inferencing output 202. In such case, the deep learning neural network 104 can be considered as having incorrectly or inaccurately performed the inferencing task on the test data candidate 106. Thus, it can be desired to retrain or refine the deep learning neural network 104 on annotated data candidates that are substantively-similar to the test data candidate 106.

As described herein, the search component 120 can identify such substantively-similar annotated data candidates, by querying the candidate-embedding dataset 702.

Indeed, if the feedback 602 indicates disapproval or rejection of the inferencing output 202, the search component 120 can query the candidate-embedding dataset 702 in search of annotated data candidates whose embeddings match or are otherwise within any suitable threshold margin of the embedding 404. As a non-limiting example, the search component 120 can search or iterate through the set of embeddings 804 so as to find p embeddings that match or are otherwise within the threshold margin of the embedding 404, for any suitable positive integer p<n.

In various aspects, the search component 120 can perform such searching or iteration using any suitable embedding comparison metric. As a non-limiting example, the search component 120 can perform such searching or iteration using cosine similarity comparison. That is, for each given embedding in the set of embeddings 804, the search component 120 can compute a cosine similarity value between that given embedding and the embedding 404, and the search component 120 can identify p of the set of embeddings 804 whose cosine similarity values exceed any suitable threshold margin (e.g., since cosine similarity increases as level of substantive similarity increases). As another non-limiting example, the search component 120 can perform such searching or iteration using Euclidean distance comparison. That is, for each given embedding in the set of embeddings 804, the search component 120 can compute a Euclidean distance value between that given embedding and the embedding 404, and the search component 120 can identify p of the set of embeddings 804 whose Euclidean distance values are below any suitable threshold margin (e.g., since Euclidean distance decreases as level of substantive similarity increases).

In any case, the search component 120 can identify p embeddings of the set of embeddings 804 that match or are otherwise sufficiently similar to the embedding 404, and whichever of the set of annotated data candidates 802 correspond to those p embeddings can be considered as collectively forming the set of identified annotated data candidates 704. Accordingly, the set of identified annotated data candidates 704 can comprise p data candidates: an identified annotated data candidate 704(1) to an identified annotated data candidate 704(p). Note that, because the embeddings of the set of identified annotated data candidates 704 can have matched or otherwise been within any suitable threshold margin of the embedding 404, each of the set of identified annotated data candidates 704 can be considered as being substantively-similar to the test data candidate 106.

Note that the search component 120 can obtain the set of identified annotated data candidates 704 after the short, limited, or temporary time period in which the test data candidate 106 is available. After all, the embedding 404 can be available, notwithstanding that the test data candidate 106 may no longer be available (e.g., the embedding 404 can be a latent vector representation that does not invoke privacy concerns).

In various embodiments, the update component 122 can electronically retrain or refine the deep learning neural network 104, based on the set of identified annotated data candidates 704. More specifically, the update component 122 can perform supervised training on the deep learning neural network 104, using the set of identified annotated data candidates 704. For example, the update component 122 can execute (e.g., using any suitable training batch size or any suitable number of training epochs) the deep learning neural network 104 on the set of identified annotated data candidates 704, thereby yielding various inferencing outputs respectively corresponding to the set of identified annotated data candidates 704. Moreover, the update component 122 can compute errors or losses (e.g., MAE, MSE, cross-entropy) between those inferencing outputs and whatever ground-truth annotations that respectively correspond to the set of identified annotated data candidates 704. Furthermore, the update component 122 can incrementally update, via backpropagation (e.g., stochastic gradient descent), trainable internal parameters (e.g., weight matrices, bias values, convolutional kernels) of the deep learning neural network 104 based on such errors or losses. In this way, the deep learning neural network 104 can be considered as being retrained or refined so as to be able to more accurately analyze data that is substantively-similar to the test data candidate 106 in the future.

Note that such retraining can be considered as supervised retraining of the deep learning neural network 104. Indeed, such supervision is why 802 and 704 are primarily referred to herein as "annotated". However, this is a mere non-limiting example for case of illustration and explanation. Rather than supervised retraining, the update component 122 can, in various aspects, instead perform any other suitable type of retraining (e.g., unsupervised retraining, reinforcement learning) on the deep learning neural network 104, based on the set of identified annotated data candidates 704. Indeed, in such cases, such retraining can be performed even in the absence of ground-truth annotations. In other words, in such cases, it can be possible that: the candidate-embedding dataset 702 contains only unannotated data candidates (e.g., each of 802 can instead be unannotated, each of 704 can instead be unannotated); the search component 120 can identify, via embedding querying, which of such unannotated data candidates are similar to the test data candidate 106; and the update component 122 can facilitate retraining of the deep learning neural network 104 based on such identified unannotated data candidates.

In any case, the search component 120 can leverage embedding querying as described herein to identify which data candidates (e.g., whether annotated or unannotated) are similar to the test data candidate 106, and the update component 122 can retrain or refine (e.g., in supervised or unsupervised fashion) the deep learning neural network 104 based on such identified data candidates. This can, in various embodiments, be performed for any suitable number of test data candidates (e.g., for any suitable number of instances of 106, for any suitable number of identified failure modes). Such embodiments can thus be considered as helping to facilitate continuous, continual, or on-going model refinement (e.g., MLops).

FIG. 10 illustrates a flow diagram of an example, non-limiting computer-implemented method 1000 that can facilitate data candidate querying via embeddings for deep learning refinement in accordance with one or more embodiments described herein. In various cases, the embedding query system 102 can facilitate the computer-implemented method 1000.

In various embodiments, act 1002 can include accessing, by a device (e.g., via 112) operatively coupled to a processor (e.g., 108), a test data candidate (e.g., 106) of a client.

In various aspects, act 1004 can include executing, by the device (e.g., via 114), an artificial intelligence (AI) model (e.g., 104) on the test data candidate, thereby yielding an inferencing output (e.g., 202).

In various instances, act 1006 can include executing, by the device (e.g., via 116), an embedder network (e.g., 402) on the test data candidate, thereby yielding an embedding (e.g., 404).

In various cases, act 1008 can include determining, by the device (e.g., via 118), whether the client has rejected the inferencing output as incorrect. If so (e.g., if the client has rejected the inferencing output as being incorrect), the computer-implemented method 1000 can proceed to act 1010. If not (e.g., if the client has accepted the inferencing output as being correct), the computer-implemented method 1000 can instead proceed back to act 1002.

In various aspects, act 1010 can include identifying, by the device (e.g., via 120) and within a candidate-embedding dataset (e.g., 702), one or more annotated data candidates (e.g., 704) that have embeddings that are within a threshold level of similarity (e.g., as measured via cosine similarity or Euclidean distance) with the embedding of the test data candidate.

In various instances, act 1012 can include retraining, by the device (e.g., via 122), the AI model using the one or more annotated data candidates. In various cases, the computer-implemented method 1000 can proceed back to act 1002.

Thus far, various embodiments have been mainly described that query embeddings (e.g., 804) to identify annotated data candidates (e.g., 704) that are substantively-similar to failure data (e.g., 106) of a deep learning model (e.g., 104) so as to retrain or refine that deep learning model. However, this is a mere non-limiting example of how embeddings can be queried. In other embodiments, when given an annotated data candidate, embeddings can be queried so as to identify currently-unannotated data candidates that are substantively-similar to that given annotated data candidate, and such currently-unannotated data candidates can be annotated based on the given annotated data candidate. In other words, embeddings can be queried so as to help streamline a data annotation process. Non-limiting aspects of such other embodiments are described with respect to FIGS. 11-14.

Figure 11:
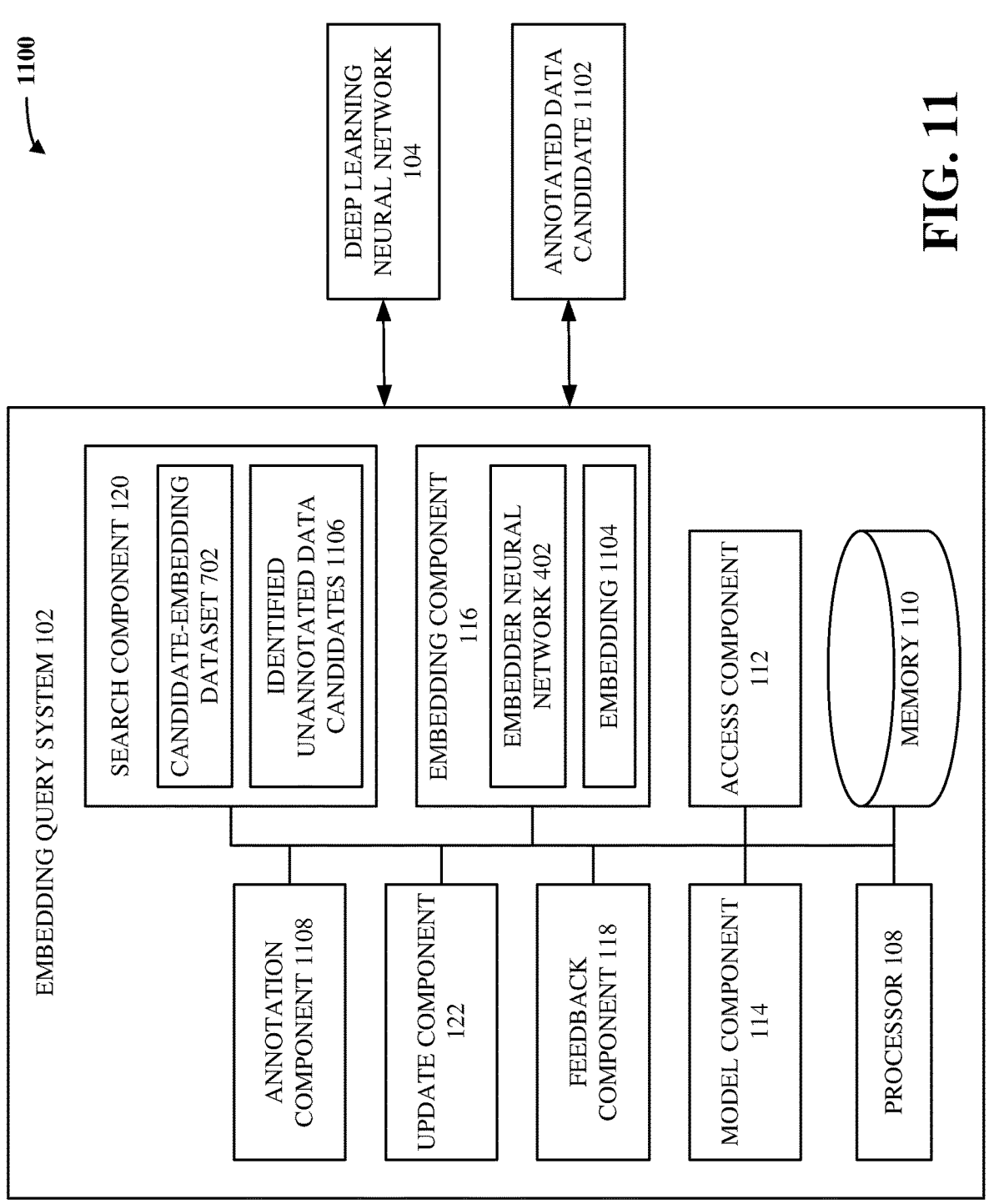
FIG. 11 illustrates a block diagram of an example, non-limiting system that facilitates data candidate querying via embeddings for deep learning refinement in accordance with one or more embodiments described herein.

FIG. 11 illustrates a block diagram of an example, non-limiting system 1100 that can facilitate data candidate querying via embeddings for deep learning refinement in accordance with one or more embodiments described herein.

Instead of the test data candidate 106, there can, in various embodiments, be an annotated data candidate 1102. In various aspects, the annotated data candidate 1102 can be any suitable data candidate (e.g., having the same format, size, or dimensionality as the test data candidate 106) for which a ground-truth annotation with respect to the inferencing task performable by the deep learning neural network 104 can be known. As a non-limiting example, the annotated data candidate 1102 can be any of the set of annotated data candidates 802.

In various aspects, the access component 112 can electronically receive, retrieve, obtain, or otherwise access, from any suitable source, the annotated data candidate 1102.

In various instances, the model component 114, the feedback component 118, and the update component 122 can refrain from taking any action with respect to the annotated data candidate 1102.

In various cases, the embedding component 116 can electronically generate an embedding 1104, by executing the embedder neural network 402 on the annotated data candidate 1102. Non-limiting aspects are described with respect to FIG. 12.

Figure 12:
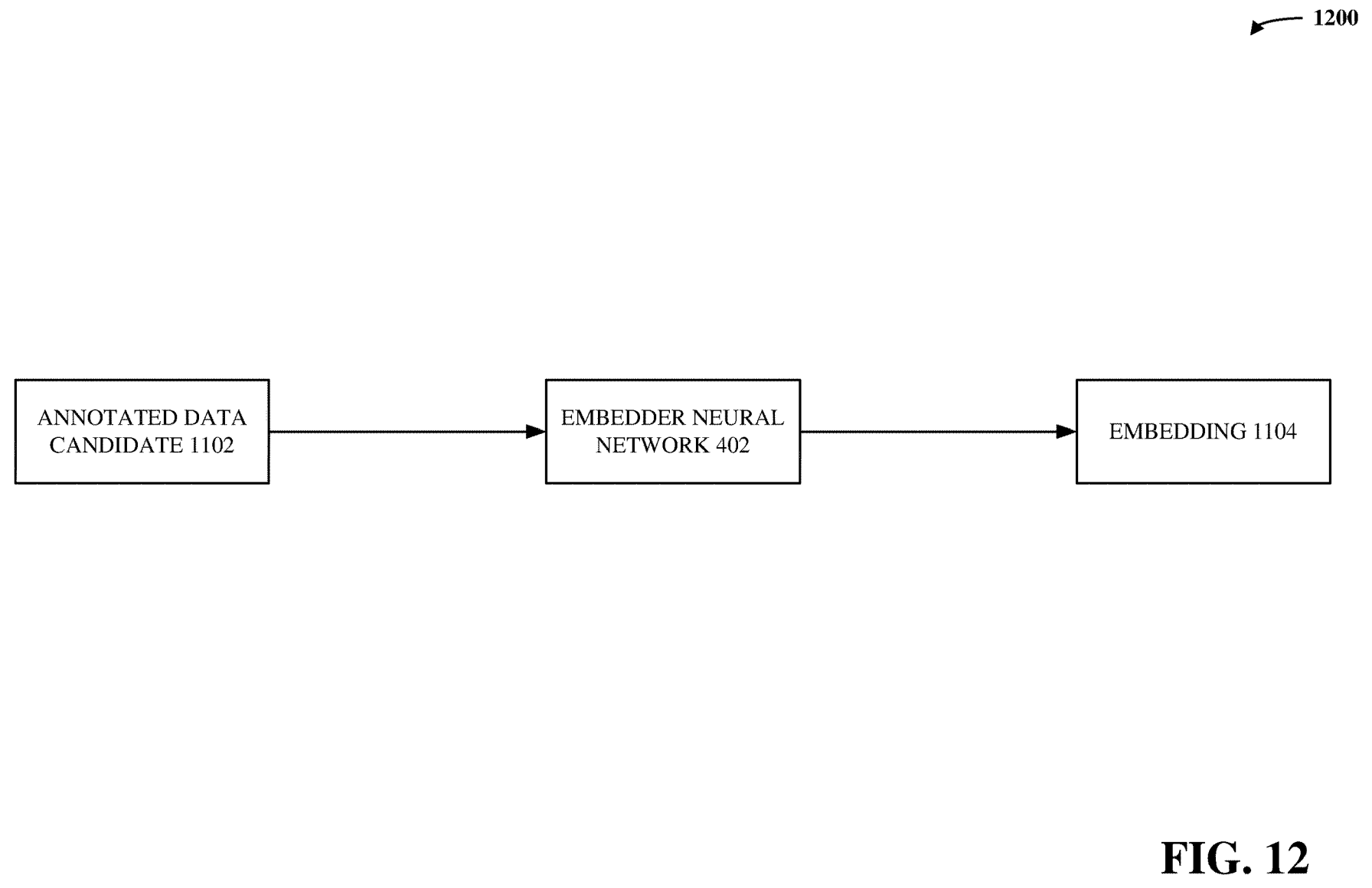

FIG. 12 illustrates an example, non-limiting block diagram 1200 showing how the embedder neural network 402 can generate the embedding 1104 in accordance with one or more embodiments described herein.

In various aspects, the embedding component 116 can electronically execute the embedder neural network 402 on the annotated data candidate 1102. In various instances, such execution can cause the embedder neural network 402 to produce the embedding 1104. In particular, the embedding component 116 can feed the annotated data candidate 1102 to the input layer of the embedder neural network 402. In various aspects, the annotated data candidate 1102 can complete a forward pass through the one or more hidden layers of the embedder neural network 402. In various cases, the output layer of the embedder neural network 402 can compute or otherwise calculate the embedding 1104 based on activation maps generated by the one or more hidden layers of the embedder neural network 402.

In any case, the embedding 1104 can be considered as a latent vector representation that the embedder neural network 402 believes or infers corresponds to the annotated data candidate 1102 (e.g., in the same way that the embedding 402 can be considered as a latent vector representation that the embedder neural network 402 believes or infers corresponds to the test data candidate 106).

Referring back to FIG. 11, the search component 120 can, in various aspects, query the candidate-embedding dataset 702 for one or more unannotated data candidates whose embeddings match or are otherwise similar to the embedding 1104. Such one or more unannotated data candidates can be referred to as a set of identified unannotated data candidates 1106. Various non-limiting aspects are described with respect to FIG. 13.

Figure 13:
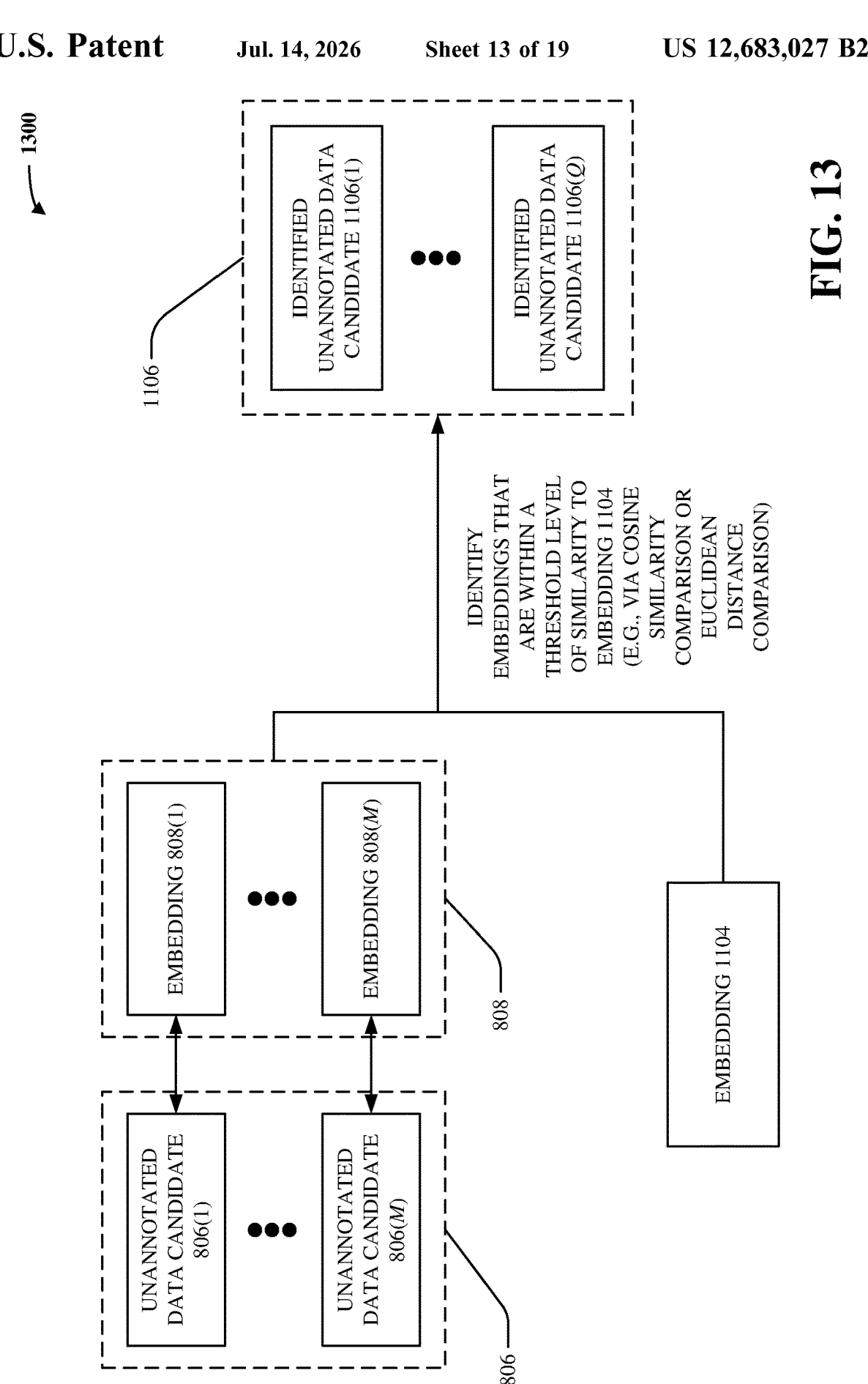
FIG. 13 illustrates an example, non-limiting block diagram showing how a candidate-embedding dataset can be queried for unannotated data candidates in accordance with one or more embodiments described herein.

FIG. 13 illustrates an example, non-limiting block diagram 1300 showing how the candidate-embedding dataset 702 can be queried for unannotated data candidates in accordance with one or more embodiments described herein.

In various aspects, as mentioned above, the annotated data candidate 1102 can have a known or available ground-truth annotation. Thus, that ground-truth annotation can be leveraged to help annotate any currently-unannotated data candidates that are substantively-similar to the annotated data candidate 1102. As described herein, the search component 120 can identify such substantively-similar unannotated data candidates, by querying the candidate-embedding dataset 702.

Indeed, the search component 120 can query the candidate-embedding dataset 702 in search of unannotated data candidates whose embeddings match or are otherwise within any suitable threshold margin of the embedding 1104. As a non-limiting example, the search component 120 can search or iterate through the set of embeddings 808 so as to find q embeddings that match or are otherwise within the threshold margin of the embedding 1104, for any suitable positive integer q<m.

As explained above, the search component 120 can perform such searching or iteration using any suitable embedding comparison metric. As a non-limiting example, the search component 120 can perform such searching or iteration using cosine similarity comparison. That is, for each given embedding in the set of embeddings 808, the search component 120 can compute a cosine similarity value between that given embedding and the embedding 1104, and the search component 120 can identify q of the set of embeddings 808 whose cosine similarity values exceed any suitable threshold margin. As another non-limiting example, the search component 120 can perform such searching or iteration using Euclidean distance comparison. That is, for each given embedding in the set of embeddings 808, the search component 120 can compute a Euclidean distance value between that given embedding and the embedding 1104, and the search component 120 can identify q of the set of embeddings 808 whose Euclidean distance values are below any suitable threshold margin.

In any case, the search component 120 can identify q embeddings of the set of embeddings 808 that match or are otherwise sufficiently similar to the embedding 1104, and whichever of the set of unannotated data candidates 806 correspond to those q embeddings can be considered as collectively forming the set of identified unannotated data candidates 1106. Accordingly, the set of identified unannotated data candidates 1106 can comprise q data candidates: an identified unannotated data candidate 1106(1) to an identified unannotated data candidate 1106($q$). Note that, because the embeddings of the set of identified unannotated data candidates 1106 can have matched or otherwise been within any suitable threshold margin of the embedding 1104, each of the set of identified unannotated data candidates 1106 can be considered as being substantively-similar to the annotated data candidate 1102.

Referring back to FIG. 11, the embedding query system 102 can, in various embodiments, comprise an annotation component 1108. In various aspects, the annotation component 1108 generate, render, or transmit any suitable electronic message indicating, suggesting, or otherwise recommending that the set of identified unannotated data candidates 1106 should be annotated commensurately or otherwise in conjunction with the annotated data candidate 1102. In other words, the annotation component 1108 can be considered as recommending that each of the set of identified unannotated data candidates 1106 can be given a respective ground-truth annotation that is the same as or otherwise similar to the ground-truth annotation of the annotated data candidate 1102. In fact, in some instances, the annotation component 1108 can even automatically generate ground-truth annotations for each of the set of identified unannotated data candidates 1106, based on the ground-truth annotation of the annotated data candidate 1102.

As a non-limiting example, suppose that the inferencing task is classification. In such case, the ground-truth annotation of the annotated data candidate 1102 can be a particular classification label. Accordingly, the annotation component 1108 can annotate each of the set of identified unannotated data candidates 1106 with that particular classification label. In other words, the annotation component 1108 can, in such cases, cause each of the set of identified unannotated data candidates 1106 to now be annotated with the same ground-truth annotation as the annotated data candidate 1102.

In this way, the annotation component 1108 can be considered as helping to case, quicken, or otherwise streamline an annotation process with respect to the set of identified unannotated data candidates 1106.

FIG. 14 illustrates a flow diagram of an example, non-limiting computer-implemented method 1400 that can facilitate data candidate querying via embeddings for deep learning refinement in accordance with one or more embodiments described herein. In various cases, the embedding query system 102 can facilitate the computer-implemented method 1400.

In various embodiments, act 1402 can include accessing, by a device (e.g., via 112) operatively coupled to a processor (e.g., 108), an annotated data candidate (e.g., 1102).

In various aspects, act 1404 can include executing, by the device (e.g., via 116), an embedder network (e.g., 402) on the annotated data candidate, thereby yielding an embedding (e.g., 1104).

In various instances, act 1406 can include identifying, by the device (e.g., via 120) and within a candidate-embedding dataset (e.g., 702), one or more unannotated data candidates (e.g., 1106) that have embeddings that are within a threshold level of similarity (e.g., as measured via cosine similarity or Euclidean distance) with the embedding of the annotated data candidate.

In various cases, act 1408 can include annotating or recommending, by the device (e.g., via 1108), that the one or more unannotated data candidates be annotated commensurately with (e.g., in the same way as, similarly to, or otherwise based on) the annotated data candidate. In various aspects, the computer-implemented method 1400 can proceed back to act 1402.

Figure 16:
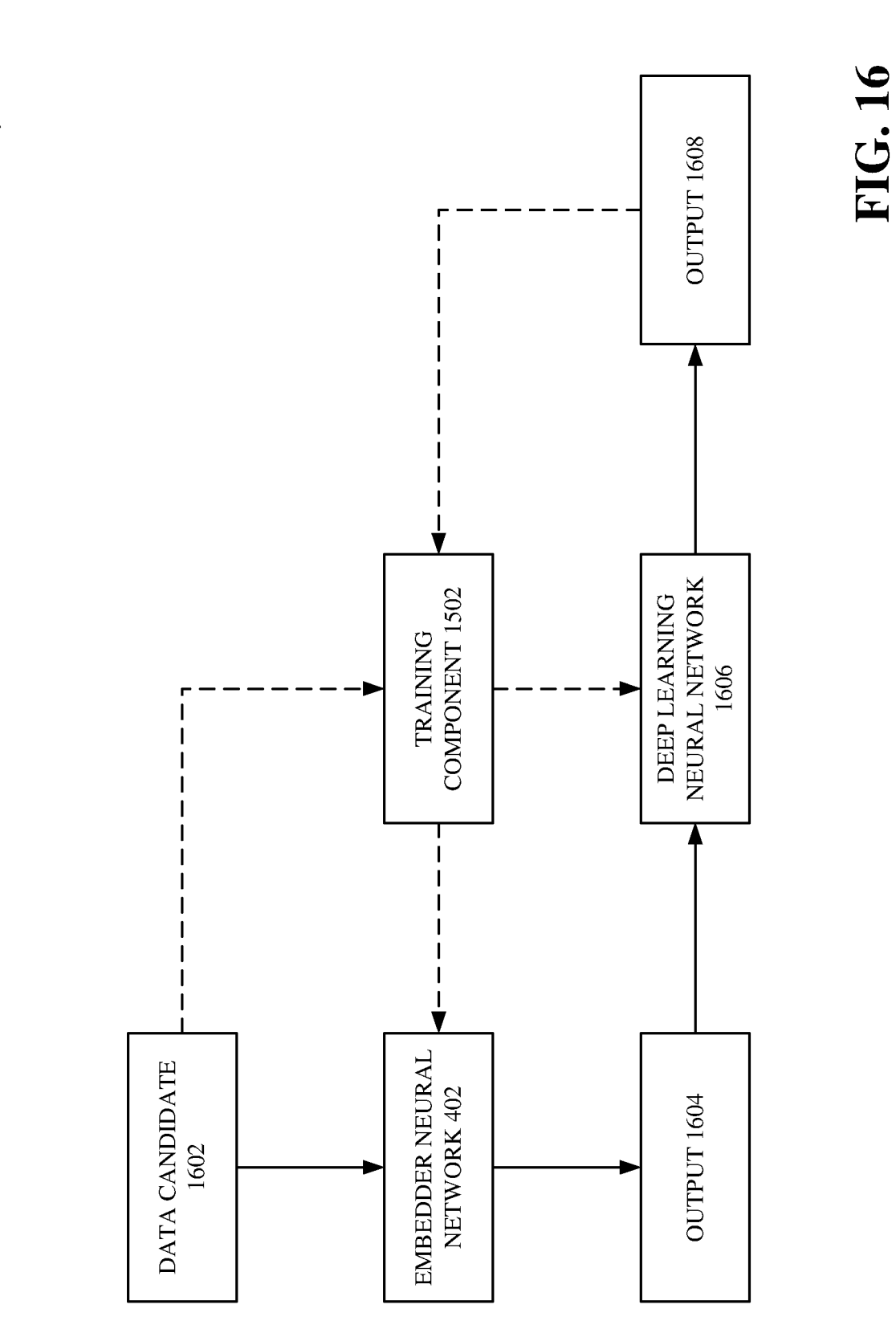
FIG. 16 illustrates an example, non-limiting block diagram showing how an embedder neural network can be trained in accordance with one or more embodiments described herein.

In order for the various embeddings described herein (e.g., 404, 804, 808, 1104) to be accurate, the embedder neural network 402 can first undergo training, as described with respect to FIGS. 15-16.

FIG. 15 illustrates a block diagram of an example, non-limiting system 1500 including a training component that can facilitate data candidate querying via embeddings for deep learning refinement in accordance with one or more embodiments described herein. As shown, the embedding query system 102 can, in various cases, comprise a training component 1502. In various instances, the training component 1502 can train the embedder neural network 402 in unsupervised fashion as part of an encoder-decoder deep learning pipeline. Various non-limiting aspects are described with respect to FIG. 16.

FIG. 16 illustrates an example, non-limiting block diagram 1600 showing how the embedder neural network 402 can be trained in accordance with one or more embodiments described herein.

In various embodiments, there can be a deep learning neural network 1606. In various aspects, the deep learning neural network 1606 can be any suitable artificial neural network that can have or otherwise exhibit any suitable internal architecture. For instance, the deep learning neural network 1606 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

Regardless of its internal architecture, the deep learning neural network 1606 can be configured to perform an inverse function as the embedder neural network 402. That is, while the embedder neural network 402 can be configured to generate embeddings (e.g., latent vectors) from inputted data candidates, the deep learning neural network 1606 can instead be configured to generate data candidates based on inputted embeddings (e.g., from inputted latent vectors).

In various aspects, the training component 1502 can leverage the deep learning neural network 1606 in order to train the embedder neural network 402, as described herein.

At the start of such training, the training component 1502 can initialize in any suitable fashion (e.g., random initialization) the trainable internal parameters (e.g., weight matrices, bias values, convolutional kernels) of the embedder neural network 402 and of the deep learning neural network 1606.

In various aspects, the training component 1502 can select, obtain, or otherwise access a data candidate 1602. In various instances, the data candidate 1602 can be any suitable data candidate having the same format, size, or dimensionality as the test data candidate 106. In some cases, the data candidate 1602 can be any of the set of annotated data candidates 802 or any of the set of unannotated data candidates 806. In other cases, however, the data candidate 1602 can come from any other source.

In any case, the embedder neural network 402 and the deep learning neural network 1606 can be serially coupled or arranged, such that the embedder neural network 402 is upstream of the deep learning neural network 1606; equivalently, the deep learning neural network 1606 can be downstream of the embedder neural network 402.

In various aspects, the training component 1502 can execute the embedder neural network 402 on the data candidate 1602. In various instances, this can cause the embedder neural network 402 to produce an output 1604. More specifically, the training component 1502 can feed the data candidate 1602 to the input layer of the embedder neural network 402. In various cases, the data candidate 1602 can complete a forward pass through the one or more hidden layers of the embedder neural network 402. Accordingly, the output layer of the embedder neural network 402 can compute or calculate the output 1604 based on activation maps produced by the one or more hidden layers of the embedder neural network 402.

Note that, in various cases, the format, size, or dimensionality of the output 1604 can be controlled or otherwise determined by the number, arrangement, or sizes of neurons or other internal parameters (e.g., convolutional kernels) that are contained in or that otherwise make up the output layer of the embedder neural network 402. Thus, the output 1604 can be forced to have any desired format, size, or dimensionality by adding, removing, or otherwise adjusting neurons or other internal parameters to, from, or within the output layer of the embedder neural network 402. Accordingly, in various aspects, the output 1604 can be forced to have a smaller (e.g., in some cases, many orders of magnitude smaller) format, size, or dimensionality than the data candidate 1602. In such case, the output 1604 can be considered as an embedding (e.g., a latent vector representation) that the embedder neural network 402 has predicted or inferred corresponds to the data candidate 1602.

Additionally, note that, if the embedder neural network 402 has so far undergone no or little training, then the output 1604 can be highly inaccurate. In other words, the output 1604 can fail to be a correct or proper embedding of the data candidate 1602 (e.g., can fail to properly encode substantive content of the data candidate 1602).

In various aspects, the training component 1502 can execute the deep learning neural network 1606 on the output 1604. In various instances, this can cause the deep learning neural network 1606 to produce an output 1608. In particular, the training component 1502 can feed the output 1604 to an input layer of the deep learning neural network 1606. In various cases, the output 1604 can complete a forward pass through one or more hidden layers of the deep learning neural network 1606. Accordingly, an output layer of the deep learning neural network 1606 can compute or calculate the output 1608 based on activation maps produced by the one or more hidden layers of the deep learning neural network 1606.

As above, note that the format, size, or dimensionality of the output 1608 can be controlled or otherwise determined by the number, arrangement, or sizes of neurons or other internal parameters (e.g., convolutional kernels) that are contained in or that otherwise make up the output layer of the deep learning neural network 1606. Thus, the output 1608 can be forced to have any desired format, size, or dimensionality by adding, removing, or otherwise adjusting neurons or other internal parameters to, from, or within the output layer of the deep learning neural network 1606. Accordingly, in various aspects, the output 1608 can be forced to have the same format, size, or dimensionality as the data candidate 1602. In such case, the output 1608 can be considered as an approximation or recreation of the data candidate 1602, as predicted or inferred by the deep learning neural network 1606.

Additionally, and just as above, note that, if the deep learning neural network 1606 has so far undergone no or little training, then the output 1608 can be highly inaccurate. That is, the output 1608 can be very different from the data candidate 1602.

In various aspects, the training component 1502 can compute an error or loss (e.g., MAE, MSE, cross-entropy) between the output 1608 and the data candidate 1602. In various instances, as shown, the training component 1502 can incrementally update the trainable internal parameters of both the embedder neural network 402 and of the deep learning neural network 1606, by performing backpropagation (e.g., stochastic gradient descent) driven by the computed error or loss. In other words, the embedder neural network 402 and the deep learning neural network 1606 can be considered as collectively forming an encoder-decoder deep learning pipeline. In such pipeline, the embedder neural network 402 can be considered as the encoder, whereas the deep learning neural network 1606 can be considered as the decoder.

In various cases, the training component 1502 can repeat the above-described training procedure for any suitable number of data candidates (e.g., for any suitable number of instances of 1602). This can ultimately cause the trainable internal parameters of the embedder neural network 402 to become iteratively optimized for accurately generating embeddings based on inputted data candidates, and this can also ultimately cause the trainable internal parameters of the deep learning neural network 1606 to become iteratively optimized for accurately recreating data candidates based on inputted embeddings. In various aspects, the training component 1502 can implement any suitable training batch sizes, any suitable training termination criterion, or any suitable error, loss, or objective function when training the embedder neural network 402 and the deep learning neural network 1606.

Although the above discussion mainly describes the embedder neural network 402 as being trained in unsupervised fashion as an encoder of an encoder-decoder pipeline, this is a mere non-limiting example for case of illustration and explanation. In various aspects, the embedder neural network 402 can be trained in any suitable fashion (e.g., supervised fashion, reinforcement learning fashion) to generate embeddings (e.g., to generate latent vector representations). Indeed, in some aspects, the embedder neural network 402 can be any suitable deep learning neural network that can have been trained in any suitable fashion to perform any suitable inferencing task (e.g., classification, segmentation, regression) on inputted data candidates, and the embeddings described herein (e.g., 404, 804, 808, 1104) can be any suitable activation maps generated by hidden layers (e.g., intermediate layers) of the embedder neural network 402.

Although the figures and the herein disclosure mainly describe various embodiments as including one instance of the embedder neural network 402, this is a mere non-limiting example for case of explanation and illustration. In various aspects, the embedding component 116 can store, maintain, control, or otherwise access a plurality of embedder neural networks (e.g., a plurality of 402). In such cases, each respective or unique embedder neural network of such plurality can be considered as learning how to encode a respective aspect or portion of substantive content of inputted data candidates. As a non-limiting example, a first embedder neural network can learn how to generate first embeddings (e.g., first latent vectors) that represent or encode a first type of substantive content of inputted data candidates, whereas a second embedder neural network can learn how to generate second embeddings (e.g., second latent vectors) that represent or encode a second type of substantive content of inputted data candidates. In embodiments where multiple embedder neural networks are implemented, multiple embeddings can be generated for each data candidate in question (e.g., multiple embeddings for 106, multiple embeddings for each of 802, multiple embeddings for each of 806, multiple embeddings for 1102), and such multiple embeddings (e.g., which can be tagged with respective identifiers) can be queried or compared as described above (e.g., via cosine similarity or Euclidean distance) to identify substantively-similar data candidates.

Furthermore, although the figures mainly depict the candidate-embedding dataset 702 as being local to the search component 120, this is a mere non-limiting example for case of illustration and explanation. In various aspects, the candidate-embedding dataset 702 can be implemented as any suitable centralized or decentralized data store that is local to the search component 120 or that is remote from the search component 120. As a non-limiting example, the candidate-embedding dataset 702 can be implemented fully or partially in a cloud computing environment.

FIG. 17 illustrates a flow diagram of an example, non-limiting computer-implemented method 1700 that can facilitate data candidate querying via embeddings for deep learning refinement in accordance with one or more embodiments described herein. In various cases, the embedding query system 102 can facilitate the computer-implemented method 1700.

In various embodiments, act 1702 can include accessing, by a device (e.g., via 112) operatively coupled to a processor (e.g., 108), a test data candidate (e.g., 106) provided by a client.

In various aspects, act 1704 can include generating, by the device (e.g., via 114) and via a first deep learning neural network (e.g., via 104), an inferencing output (e.g., 202) based on the test data candidate.

In various instances, act 1706 can include generating, by the device (e.g., via 116) and via at least one second deep learning neural network (e.g., 402), at least one embedding (e.g., 404) based on the test data candidate.

In various cases, act 1708 can include accessing, by the device (e.g., via 118), feedback (e.g., 602) indicating whether the client accepts or rejects the inferencing output.

In various aspects, act 1710 can include identifying, by the device (e.g., via 120), in response to the feedback indicating that the client rejects the inferencing output, and in a candidate-embedding dataset (e.g., 702), one or more data candidates (e.g., 704) whose embeddings are within a threshold level of similarity to the at least one embedding.

In various instances, act 1712 can include retraining, by the device (e.g., via 122), the first deep learning neural network based on the one or more data candidates.

Although not explicitly shown in FIG. 17, the candidate-embedding dataset can be stored in a cloud computing environment or in a non-cloud computing environment.

Although not explicitly shown in FIG. 17, the test data candidate can be a scanned medical image of a medical patient, the inferencing output can be a classification, segmentation, or regression based on the scanned medical image, and the at least one embedding can be at least one vector having a smaller dimensionality than the scanned medical image.

Although not explicitly shown in FIG. 17, the device can identify the one or more data candidates via cosine similarity comparison or Euclidean distance comparison.

Although not explicitly shown in FIG. 17, the computer-implemented method 1700 can comprise: training, by the device (e.g., via 1502), the at least one second deep learning neural network in unsupervised fashion or in supervised fashion.

In various aspects, various embodiments described herein can be implemented as a computer program product for facilitating data candidate querying via embeddings for deep learning refinement. In various instances, the computer program product can comprise a non-transitory computer-readable memory (e.g., 110) having program instructions embodied therewith. In various cases, the program instructions can be executable by a processor (e.g., 108) to cause the processor to: access (e.g., via 112) an annotated data candidate (e.g., 1102); generate (e.g., via 116), via at least one deep learning neural network (e.g., 402), at least one embedding (e.g., 1104) based on the annotated data candidate; identify (e.g., via 120), in a candidate-embedding dataset (e.g., 702), one or more unannotated data candidates (e.g., 1106) whose embeddings are within a threshold level of similarity to the at least one embedding; and generate (e.g., via 1108) an electronic message recommending that the one or more unannotated data candidates be annotated in accordance with the annotated data candidate. In various aspects, the candidate-embedding dataset can be stored in a cloud computing environment or in a non-cloud computing environment. In various instances, the annotated data candidate can be a scanned medical image having a corresponding ground-truth classification, ground-truth segmentation, or ground-truth regression, and the at least one embedding can be at least one vector having a smaller dimensionality than the scanned medical image. In various cases, the processor can identify the one or more unannotated data candidates via cosine similarity comparison or Euclidean distance comparison. In various aspects, the program instructions can be further executable to cause the processor to: train (e.g., via 1502) the at least one deep learning neural network in unsupervised fashion or in a supervised fashion.

Although the herein disclosure has mainly described various embodiments as performing embedding querying on "data candidates" so as to refine deep learning neural networks that perform "inferencing tasks" on those data candidates, this is a mere non-limiting example to explain implementation of various embodiments without loss of generality. In various aspects, however, various embodiments described herein can be specifically implemented in a medical imaging operational context.

In particular, a data candidate (e.g., 106, any of 802, any of 806, 1102) can be any suitable medical image (e.g., can be a two-dimensional pixel array or a three-dimensional voxel array) that can visually depict or illustrate any suitable anatomical structure (e.g., organ, tissue, body part, bodily fluid) of any suitable medical patient (e.g., human, animal, or otherwise) and that can be scanned, captured, or otherwise generated by any suitable medical imaging scanner (e.g., CT scanner, MRI scanner, PET scanner, X-ray scanner, ultrasound scanner). In such case, the deep learning neural network 104 can be configured to generate any suitable classifications, segmentation masks, or regression outputs based on inputted medical images. Such classifications, segmentation masks, or regression outputs can be leveraged by a medical professional to help determine diagnoses or prognoses for medical patients. Accordingly, such classifications, segmentation masks, or regression outputs can, in some embodiments, be referred to as diagnostic or prognostic outputs. Moreover, in such case, the candidate-embedding dataset 702 can be considered as an image-embedding dataset that correlates, links, or otherwise maps various (e.g., pre-stored) medical images to respective embeddings (e.g., to respective latent vectors).

Thus, when given any particular medical image (e.g., 106) that the deep learning neural network 104 has failed to accurately analyze, an embedding (e.g., 404) for that particular medical image can be generated by the embedder neural network 402, one or more other medical images (e.g., 704) whose embeddings are sufficiently close to that of the particular medical image can be identified in the candidate-embedding dataset 702, and the deep learning neural network 104 can be retrained or refined (e.g., in supervised or unsupervised fashion) on such identified medical images.

Similarly, when given any specific medical image (e.g., 1102) that is already annotated, an embedding (e.g., 1104) for that specific medical image can be generated by the embedder neural network 402, one or more other medical images (e.g., 1106) that are not yet annotated and whose embeddings are sufficiently close to that of the specific medical image can be identified in the candidate-embedding dataset 702, and such identified medical images can be annotated based on that specific medical image (e.g., can be given a same or similar ground-truth annotation as that specific medical image). Accordingly, such newly-annotated medical images can thus be used to train any suitable deep learning neural network (e.g., 104).

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by $f(2)=confidence (class)$. Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

Figure 18:
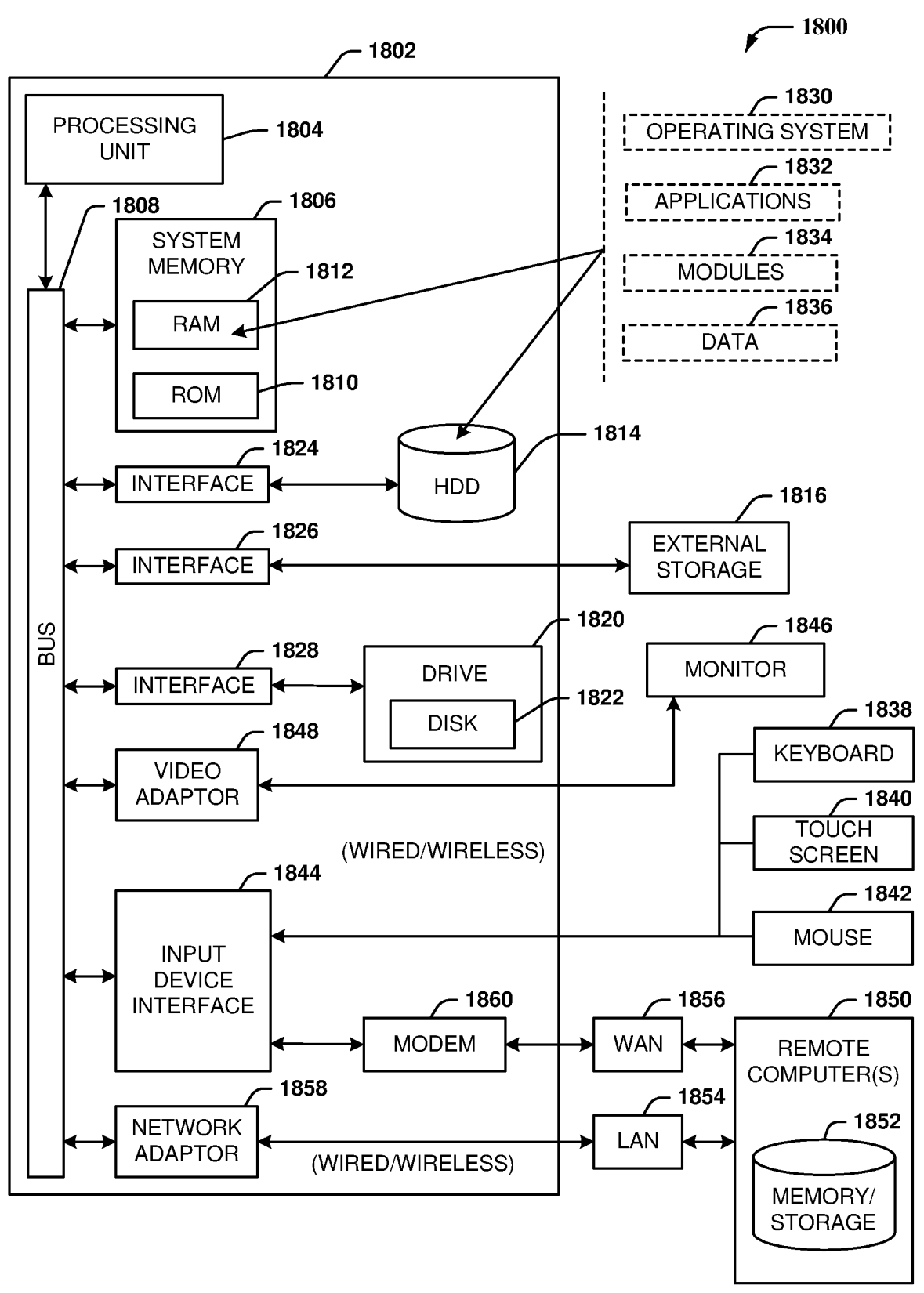
FIG. 18 illustrates a block diagram of an example, non-limiting operating environment in which one or more embodiments described herein can be facilitated.

In order to provide additional context for various embodiments described herein, FIG. 18 and the following discussion are intended to provide a brief, general description of a suitable computing environment 1800 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that various aspects can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 18, the example environment 1800 for implementing various embodiments of the aspects described herein includes a computer 1802, the computer 1802 including a processing unit 1804, a system memory 1806 and a system bus 1808. The system bus 1808 couples system components including, but not limited to, the system memory 1806 to the processing unit 1804. The processing unit 1804 can be any of various commercially available processors. Dual microprocessors and other multi-processor architectures can also be employed as the processing unit 1804.

The system bus 1808 can be any of several types of bus structure that can further interconnect to a memory bus (with or without a memory controller), a peripheral bus, and a local bus using any of a variety of commercially available bus architectures. The system memory 1806 includes ROM 1810 and RAM 1812. A basic input/output system (BIOS) can be stored in a non-volatile memory such as ROM, erasable programmable read only memory (EPROM), EEPROM, which BIOS contains the basic routines that help to transfer information between elements within the computer 1802, such as during startup. The RAM 1812 can also include a high-speed RAM such as static RAM for caching data.

The computer 1802 further includes an internal hard disk drive (HDD) 1814 (e.g., EIDE, SATA), one or more external storage devices 1816 (e.g., a magnetic floppy disk drive (FDD) 1816, a memory stick or flash drive reader, a memory card reader, etc.) and a drive 1820, e.g., such as a solid state drive, an optical disk drive, which can read or write from a disk 1822, such as a CD-ROM disc, a DVD, a BD, etc. Alternatively, where a solid state drive is involved, disk 1822 would not be included, unless separate. While the internal HDD 1814 is illustrated as located within the computer 1802, the internal HDD 1814 can also be configured for external use in a suitable chassis (not shown). Additionally, while not shown in environment 1800, a solid state drive (SSD) could be used in addition to, or in place of, an HDD 1814. The HDD 1814, external storage device(s) 1816 and drive 1820 can be connected to the system bus 1808 by an HDD interface 1824, an external storage interface 1826 and a drive interface 1828, respectively. The interface 1824 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1802, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1812, including an operating system 1830, one or more application programs 1832, other program modules 1834 and program data 1836. All or portions of the operating system, applications, modules, or data can also be cached in the RAM 1812. The systems and methods described herein can be implemented utilizing various commercially available operating systems or combinations of operating systems.

Computer 1802 can optionally comprise emulation technologies. For example, a hypervisor (not shown) or other intermediary can emulate a hardware environment for operating system 1830, and the emulated hardware can optionally be different from the hardware illustrated in FIG. 18. In such an embodiment, operating system 1830 can comprise one virtual machine (VM) of multiple VMs hosted at computer 1802. Furthermore, operating system 1830 can provide runtime environments, such as the Java runtime environment or the .NET framework, for applications 1832. Runtime environments are consistent execution environments that allow applications 1832 to run on any operating system that includes the runtime environment. Similarly, operating system 1830 can support containers, and applications 1832 can be in the form of containers, which are lightweight, standalone, executable packages of software that include, e.g., code, runtime, system tools, system libraries and settings for an application.

Further, computer 1802 can be enable with a security module, such as a trusted processing module (TPM). For instance with a TPM, boot components hash next in time boot components, and wait for a match of results to secured values, before loading a next boot component. This process can take place at any layer in the code execution stack of computer 1802, e.g., applied at the application execution level or at the operating system (OS) kernel level, thereby enabling security at any level of code execution.

A user can enter commands and information into the computer 1802 through one or more wired/wireless input devices, e.g., a keyboard 1838, a touch screen 1840, and a pointing device, such as a mouse 1842. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1804 through an input device interface 1844 that can be coupled to the system bus 1808, but can be connected by other interfaces, such as a parallel port, an IEEE 1394 serial port, a game port, a USB port, an IR interface, a BLUETOOTH® interface, etc.

A monitor 1846 or other type of display device can be also connected to the system bus 1808 via an interface, such as a video adapter 1848. In addition to the monitor 1846, a computer typically includes other peripheral output devices (not shown), such as speakers, printers, etc.

The computer 1802 can operate in a networked environment using logical connections via wired or wireless communications to one or more remote computers, such as a remote computer(s) 1850. The remote computer(s) 1850 can be a workstation, a server computer, a router, a personal computer, portable computer, microprocessor-based entertainment appliance, a peer device or other common network node, and typically includes many or all of the elements described relative to the computer 1802, although, for purposes of brevity, only a memory/storage device 1852 is illustrated. The logical connections depicted include wired/wireless connectivity to a local area network (LAN) 1854 or larger networks, e.g., a wide area network (WAN) 1856. Such LAN and WAN networking environments are commonplace in offices and companies, and facilitate enterprise-wide computer networks, such as intranets, all of which can connect to a global communications network, e.g., the Internet.

When used in a LAN networking environment, the computer 1802 can be connected to the local network 1854 through a wired or wireless communication network interface or adapter 1858. The adapter 1858 can facilitate wired or wireless communication to the LAN 1854, which can also include a wireless access point (AP) disposed thereon for communicating with the adapter 1858 in a wireless mode.

When used in a WAN networking environment, the computer 1802 can include a modem 1860 or can be connected to a communications server on the WAN 1856 via other means for establishing communications over the WAN 1856, such as by way of the Internet. The modem 1860, which can be internal or external and a wired or wireless device, can be connected to the system bus 1808 via the input device interface 1844. In a networked environment, program modules depicted relative to the computer 1802 or portions thereof, can be stored in the remote memory/storage device 1852. It will be appreciated that the network connections shown are example and other means of establishing a communications link between the computers can be used.

When used in either a LAN or WAN networking environment, the computer 1802 can access cloud storage systems or other network-based storage systems in addition to, or in place of, external storage devices 1816 as described above, such as but not limited to a network virtual machine providing one or more aspects of storage or processing of information. Generally, a connection between the computer 1802 and a cloud storage system can be established over a LAN 1854 or WAN 1856 e.g., by the adapter 1858 or modem 1860, respectively. Upon connecting the computer 1802 to an associated cloud storage system, the external storage interface 1826 can, with the aid of the adapter 1858 or modem 1860, manage storage provided by the cloud storage system as it would other types of external storage. For instance, the external storage interface 1826 can be configured to provide access to cloud storage sources as if those sources were physically connected to the computer 1802.

The computer 1802 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

FIG. 19 is a schematic block diagram of a sample computing environment 1900 with which the disclosed subject matter can interact. The sample computing environment 1900 includes one or more client(s) 1910. The client(s) 1910 can be hardware or software (e.g., threads, processes, computing devices). The sample computing environment 1900 also includes one or more server(s) 1930. The server(s) 1930 can also be hardware or software (e.g., threads, processes, computing devices). The servers 1930 can house threads to perform transformations by employing one or more embodiments as described herein, for example. One possible communication between a client 1910 and a server 1930 can be in the form of a data packet adapted to be transmitted between two or more computer processes. The sample computing environment 1900 includes a communication framework 1950 that can be employed to facilitate communications between the client(s) 1910 and the server(s) 1930. The client(s) 1910 are operably connected to one or more client data store(s) 1920 that can be employed to store information local to the client(s) 1910. Similarly, the server (s) 1930 are operably connected to one or more server data store(s) 1940 that can be employed to store information local to the servers 1930.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multi-processor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:

a memory configured to store computer-executable components; and a processor that executes the computer-executable components that:

generates, using a first deep learning neural network performing an inferencing task, an inferencing output based on a client data candidate provided by a client, wherein the client data candidate comprises medical image data of a medical patient, wherein the first deep learning neural network has previously been trained to perform the inferencing task using a set of training data candidates, wherein the client data candidate has a privacy restriction that limits access by the first deep learning neural network and a second deep learning neural network to the client data candidate for a defined time period to perform the inferencing task;

generates, via the second deep learning neural network during the defined time period, a first embedding based on the client data candidate, wherein the first embedding is a vectorized representation of the client data candidate that is not decipherable by the system, the first deep learning neural network, nor the second deep learning neural network to obtain the client data candidate;

receives, from the client, after the defined time period, feedback indicating that the inferencing output is faulty;

identifies, from a candidate-embedding dataset comprising data candidates having respective second embeddings generated by the second deep learning neural network, one or more data candidates having respective second embeddings that are within a threshold level of similarity to the first embedding based on at least one metric, wherein in the data candidates have respective ground truth annotations associated with the inferencing task; and retrains, using the one or more data candidates, the first deep learning neural network to perform the inferencing task.

2. The system of claim 1, wherein the candidate-embedding dataset is stored in a cloud computing environment.

3. The system of claim 1, wherein the candidate-embedding dataset is stored in a non-cloud computing environment.

4. The system of claim 1, wherein the inferencing output is a classification, segmentation, or regression based on the medical image data, and wherein the vectorized representation has a smaller dimensionality than the medical image data.

5. The system of claim 1, wherein the at least one metric comprises at least one of a cosine similarity or a Euclidean distance.

6. The system of claim 1, wherein the at least one of the computer-executable components further:

trains the second deep learning neural network in an unsupervised fashion to generate embeddings of the data candidates.

7. The system of claim 1, wherein the at least one of the computer-executable components further:

trains the second deep learning neural network in a supervised fashion to generate embeddings of the data candidates.

8. A computer-implemented method, comprising:

generating, by a system comprising a processor, using a first deep learning neural network performing an inferencing task, an inferencing output based on a client data candidate provided by a client, wherein the client data candidate comprises medical image data of a medical patient, wherein the first deep learning neural network has previously been trained to perform the inferencing task using a set of training data candidates, wherein the client data candidate has a privacy restriction that limits access by the first deep learning neural network and a second deep learning neural network to the client data candidate for a defined time period to perform the inferencing task;

generating, by the system, using the second deep learning neural network during the defined time period, a first embedding based on the client data candidate, wherein the first embedding is a vectorized representation of the client data candidate that is not decipherable by the system, the first deep learning neural network, nor the second deep learning neural network to obtain the client data candidate;

receiving, by the system, from the client, after the defined time period, feedback indicating that the inferencing output is faulty;

identifying, by the system, from a candidate-embedding dataset comprising data candidates having respective second embeddings generated by the second deep learning neural network, one or more data candidates having respective second embeddings that are within a threshold level of similarity to the first embedding based on at least one metric, wherein in the data candidates have respective ground truth annotations associated with the inferencing task; and retraining, by the system, using the one or more data candidates, the first deep learning neural network to perform the inferencing task.

9. The computer-implemented method of claim 8, wherein the candidate-embedding dataset is stored in a cloud computing environment.

10. The computer-implemented method of claim 8, wherein the candidate-embedding dataset is stored in a non-cloud computing environment.

11. The computer-implemented method of claim 8, wherein the inferencing output is a classification, segmentation, or regression based on the medical image data, and wherein the vectorized representation has a smaller dimensionality than the medical image data.

12. The computer-implemented method of claim 8, wherein the at least one metric comprises at least one of a cosine similarity or Euclidean distance.

13. The computer-implemented method of claim 8, further comprising:

training, by the system, the second deep learning neural network in an unsupervised fashion to generate embeddings of the data candidates.

14. The computer-implemented method of claim 8, further comprising:

training, by the system, the second deep learning neural network in a supervised fashion to generate embeddings of the data candidates.

15. A computer program product comprising a non-transitory computer-readable memory having program instructions embodied therewith, the program instructions executable by a processor of a system to cause the processor to:

generate, using a first deep learning neural network performing an inferencing task, an inferencing output based on a client data candidate provided by a client, wherein the client data candidate comprises medical image data of a medical patient, wherein the first deep learning neural network has previously been trained to perform the inferencing task using a set of training data candidates, wherein the client data candidate has a privacy restriction that limits access by the first deep learning neural network and a second deep learning neural network to the client data candidate for a defined time period to perform the inferencing task;

generate, using the second deep learning neural network during the defined time period, a first embedding based on the client data candidate, wherein the first embedding is a vectorized representation of the client data candidate that is not decipherable by the system, the first deep learning neural network, nor the second deep learning neural network to obtain the client data candidate;

identify, from a candidate-embedding dataset comprising data candidates having respective second embeddings generated by the second deep learning neural network, one or more data candidates having respective second embeddings that are within a threshold level of similarity to the first embedding based on at least one metric, wherein in the data candidates have respective ground truth annotations associated with the inferencing task; and retrain, using the one or more data candidates, the first deep learning neural network to perform the inferencing task.

16. The computer program product of claim 15, wherein the candidate-embedding dataset is stored in a cloud computing environment.

17. The computer program product of claim 15, wherein the inferencing output is a classification, segmentation, or regression based on the medical image data, and wherein the vectorized representation has a smaller dimensionality than the medical image data.

18. The computer program product of claim 15, wherein the at least one metric comprises at least one of a cosine similarity or Euclidean distance.

19. The computer program product of claim 15, wherein the program instructions are further executable to cause the processor to:

train the second deep learning neural network in an unsupervised fashion to generate embeddings of the data candidates.

20. The computer program product of claim 15, wherein the program instructions are further executable to cause the processor to:

train the second deep learning neural network in a supervised fashion to generate embeddings of the data candidates.

* * * * *